(12) United States Patent
Amemiya et al.

(10) Patent No.: US 8,933,613 B2
(45) Date of Patent: Jan. 13, 2015

(54) ULTRASONIC TRANSDUCER DRIVING CIRUIT AND ULTRASONIC IMAGE DISPLAY APPARATUS

(75) Inventors: Shinichi Amemiya, Tokyo (JP); Bruno Haider, Ballston Lake, NY (US); Krishnakumar Sundaresan, Clifton Park, NY (US)

(73) Assignee: General Electric Company, Schenectady, NY (US)

( * ) Notice: Subject to any disclaimer, the term of this patent is extended or adjusted under 35 U.S.C. 154(b) by 371 days.

(21) Appl. No.: 13/284,156

(22) Filed: Oct. 28, 2011

(65) Prior Publication Data

US 2013/0104658 A1    May 2, 2013

(51) Int. Cl.
  *B06B 1/02*    (2006.01)
  *G01N 29/34*    (2006.01)

(52) U.S. Cl.
  CPC .............. *B06B 1/0215* (2013.01); *G01N 29/34* (2013.01)
  USPC ........................ 310/334; 310/316.03; 310/317

(58) Field of Classification Search
  CPC .... G01N 29/34; B06B 1/0207; B06B 1/0215; H01L 41/09
  USPC ...................... 310/322, 334, 335, 316.03, 317
  See application file for complete search history.

(56) References Cited

U.S. PATENT DOCUMENTS

| | | | |
|---|---|---|---|
| 7,351,204 B2 | 4/2008 | Amemiya | |
| 7,777,394 B2 | 8/2010 | Amemiya | |
| 7,855,609 B2 | 12/2010 | Amemiya | |
| 8,009,072 B2 | 8/2011 | Rigby et al. | |
| 2008/0066552 A1 | 3/2008 | Amemiya | |
| 2009/0206676 A1* | 8/2009 | Chu et al. ....................... | 307/106 |
| 2010/0019833 A1 | 1/2010 | Zang et al. | |
| 2010/0041997 A1 | 2/2010 | Amemiya et al. | |
| 2010/0331703 A1 | 12/2010 | Amemiya | |
| 2011/0060225 A1 | 3/2011 | Cogan et al. | |

FOREIGN PATENT DOCUMENTS

JP    2009-101072    5/2009

OTHER PUBLICATIONS

Search Report and Written Opinion from PCT Application No. PCT/US2012/060476 dated Sep. 17, 2013.

* cited by examiner

*Primary Examiner* — Derek Rosenau

(74) *Attorney, Agent, or Firm* — Armstrong Teasdale LLP

(57) ABSTRACT

An ultrasonic transducer driving circuit configured to supply an output current and/or an output voltage to an output line for driving an ultrasonic transducer is provided. The ultrasonic transducer driving circuit includes a first current discharge circuit configured to allow a current arising from electric charges accumulated in the ultrasonic transducer to flow from the output line to ground when the output line is at a positive voltage, and a second current discharge circuit configured to allow the current arising from the electric charges accumulated in the ultrasonic transducer to flow from ground to the output line when the output line is at a negative voltage. The first current discharge circuit and the second current discharge circuit are controlled based on the output current and/or the output voltage.

6 Claims, 23 Drawing Sheets

ULTRASONIC TRANSDUCER DRIVING CIRUIT AND ULTRASONIC IMAGE DISPLAY APPARATUS

BACKGROUND OF THE INVENTION

The embodiments described herein relate to an ultrasonic transducer driving circuit and ultrasonic image display apparatus.

An ultrasonic transducer driving circuit is a circuit that outputs pulses comprised of positive pulses and negative pulses to an output line toward an ultrasonic transducer and drives the ultrasonic transducer. As this kind of ultrasonic transducer driving circuit, a voltage output type circuit that controls an output voltage and supplies an electrical current for driving an ultrasonic transducer is described in, for example, Japanese Unexamined Patent Publication No. 2009-101072. In particular, the voltage output type circuit comprises a positive voltage output circuit which outputs a positive voltage to the above-mentioned output line and a negative voltage output circuit which outputs a negative voltage to the above-mentioned output line. In this ultrasonic transducer driving circuit, when negative pulses are to be generated from a state in which the above-mentioned output line is at a positive voltage, the above-mentioned negative voltage output circuit is triggered to operate; and when positive pulses are to be generated from a state in which the above-mentioned output line is at a negative voltage, the above-mentioned positive voltage output circuit is triggered to operate.

When the above-mentioned negative voltage output circuit is triggered to operate when generating negative pulses from a state in which the above-mentioned output line is supplied with a positive voltage, a current arising from electric charges which have been charged in the above-mentioned ultrasonic transducer flows in this negative voltage output circuit for a certain period of time and power is consumed. In turn, when the above-mentioned positive voltage output circuit is triggered to operate when generating positive pulses from a state in which the above-mentioned output line is at a negative voltage, a current arising from electric charges which have been charged in the above-mentioned ultrasonic transducer flows in this positive voltage output circuit for a certain period of time and power is consumed. Therefore, reducing power consumption becomes a problem.

BRIEF DESCRIPTION OF THE INVENTION

In one aspect, an ultrasonic transducer driving circuit supplies an output current or an output voltage to an output line for driving an ultrasonic transducer. The ultrasonic transducer driving circuit includes a first current discharge circuit that, when the output line is at a positive voltage, allows a current arising from electric charges accumulated in the ultrasonic transducer to flow from the output line to ground and a second current discharge circuit that, when the output line is at a negative voltage, allows the current arising from electric charges accumulated in the ultrasonic transducer to flow from ground to the output line. The operations of the first and the second current discharge circuits are controlled in accordance with the output current or the output voltage.

Here, the output current or the output voltage is a current or a voltage of an output line of the ultrasonic transducer driving circuit.

In another aspect, an ultrasonic transducer driving circuit includes a current output type circuit that controls an output current for driving an ultrasonic transducer and a current control unit that outputs a current to the current output type circuit for controlling the output current. The current output type circuit includes a first current discharge circuit that, when the output line is at a positive voltage, allows a current arising from electric charges accumulated in the ultrasonic transducer to flow from the output line to ground and a second current discharge circuit that, when the output line is at a negative voltage, allows the current arising from electric charges accumulated in the ultrasonic transducer to flow from ground to the output line. The operations of the first current discharge circuit and the second current discharge circuit are controlled by a current from the current control unit.

Here the output current is a current of an output line of the current output type circuit.

In yet another aspect, an ultrasonic transducer driving circuit includes a voltage output type circuit that controls an output voltage and supplies an electrical current to an output line for driving an ultrasonic transducer and a first current discharge circuit and a second current discharge circuit connected to the output line. The first current discharge circuit is a circuit that, when the output line is at a positive voltage, allows a current arising from electric charges accumulated in the ultrasonic transducer to flow from the output line to ground and the second current discharge circuit is a circuit that, when the output line is at a negative voltage, allows the current arising from electric charges accumulated in the ultrasonic transducer to flow from ground to the output line. The operations of the first and second current discharge circuits are controlled by the voltage difference between the output line and the output of the voltage output type circuit.

Here, the output voltage is a voltage of an output line of the voltage output type circuit.

In yet another aspect, an ultrasonic transducer driving circuit includes a voltage output type circuit that controls an output voltage and supplies an electrical current to an output line for driving an ultrasonic transducer and a buffer amplifier that is provided between this voltage output type circuit and the ultrasonic transducer and takes input of an output voltage of the voltage output type circuit. The buffer amplifier includes a first push-pull circuit having a first transistor and a second transistor connected to an output line of the buffer amplifier and a second push-pull circuit having a third transistor and a fourth transistor connected between the output line of the buffer amplifier and a ground. A voltage having a predetermined voltage difference relative to the output voltage of the voltage output type circuit is input to each of the transistors constituting the first push-pull circuit and the second push-pull circuit. The predetermined voltage difference is larger for the fourth transistor than for the second transistor, so that, when the output line of the buffer amplifier is at a positive voltage, the fourth transistor, of the second transistor and the fourth transistor, turns into an ON state in accordance with an output voltage of the voltage output type circuit, thereby allowing the current arising from electric charges accumulated in the ultrasonic transducer to flow from the output line to ground. The predetermined voltage difference is also larger for the third transistor than for the first transistor, so that, when the output line of the buffer amplifier is at a negative voltage, the third transistor, of the first transistor and the third transistor, turns into an ON state in accordance with an output voltage of the voltage output type circuit, thereby allowing the current arising from electric charges accumulated in the ultrasonic transducer to flow from ground to the output line.

Here, the output voltage is a voltage of an output line of the voltage output type circuit.

A further aspect includes an ultrasonic image display apparatus having an ultrasonic transducer driving circuit pertaining to any of the aspects described above.

According to the aspects described above, when the output line is at a positive voltage, the current arising from electric charges accumulated in the ultrasonic transducer flows from the output line to ground. When the output line is at a negative voltage, the current arising from electric charges accumulated in the ultrasonic transducer flows from ground to the output line. Thereby, power consumption can be reduced.

DETAILED DESCRIPTION OF THE INVENTION

In the following, embodiments of the present invention will be described in detail based on the drawings.

First Embodiment

Figure 1:
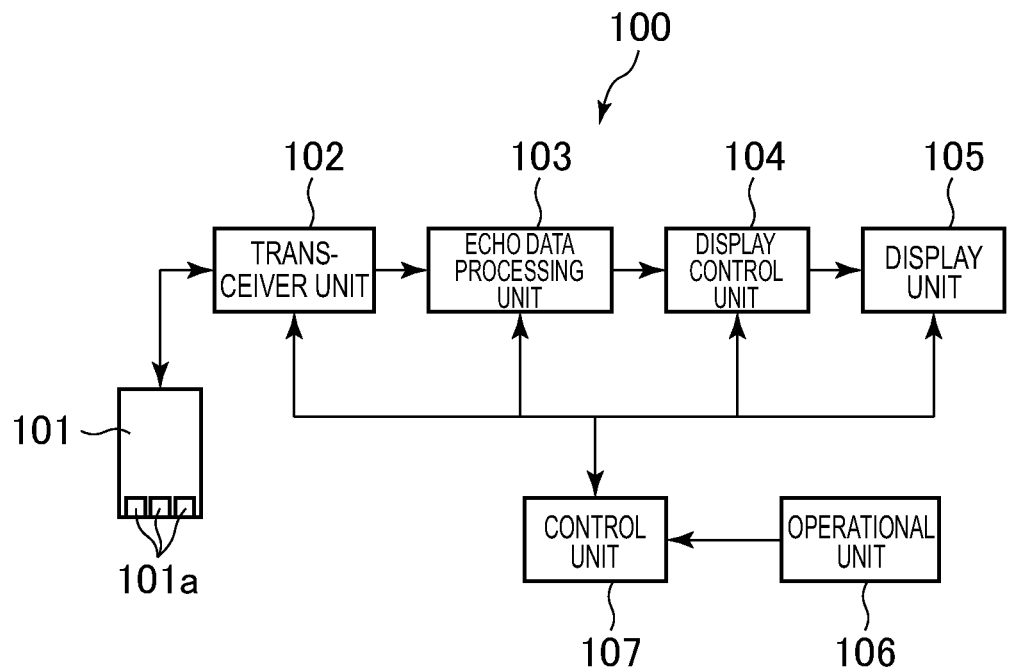
FIG. 1 is a block diagram showing an exemplary embodiment of an ultrasonic image display apparatus.

To begin with, a first embodiment is described based on FIGS. 1-8. As shown in FIG. 1, an ultrasonic image display apparatus 100 includes an ultrasonic probe 101, a transceiver unit 102, an echo data processing unit 103, a display control unit 104, a display unit 105, an operational unit 106, and a control unit 107.

The ultrasonic probe 101 is provided with a plurality of ultrasonic transducers 101a for transmitting and receiving ultrasonic waves.

Figure 2:
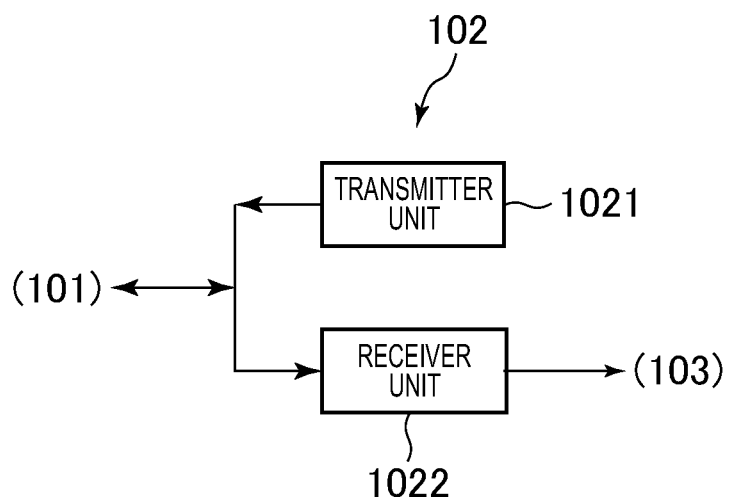
FIG. 2 is a block diagram showing a transceiving section of the ultrasonic image display apparatus shown in FIG. 1.

The transceiver unit 102 includes a transmitter unit 1021 and a receiver unit 1022, as shown in FIG. 2. The transmitter unit 1021 supplies an electric signal for transmitting ultrasonic waves under predetermined scanning conditions to the ultrasonic transducers 101a, based on a control signal from the control unit 107. The transmitter unit 1021 includes ultrasonic transducer driving circuits 1 that supply an electric signal for driving the ultrasonic transducers 101a and causing them to transmit ultrasonic waves (not shown in FIG. 2; see FIG. 3). Further description about the ultrasonic transducer driving circuits 1 will be provided later.

The receiver unit 1022 performs signal processing such as A/D conversion, phasing and addition, etc. on an echo signal received by the ultrasonic probe 2 and outputs resulting echo data to the echo data processing unit 103.

The echo data processing unit 103 performs processing for producing an ultrasonic image on echo data which has been input from the transceiver unit 102. For example, the echo data processing unit 103 performs B-mode processing such as logarithmic compression and envelope detection and Doppler processing such as quadrature detection and filtering.

The display control unit 104 performs scan conversion of data obtained by the echo data processing unit 103 using a scan converter and produces ultrasonic image data. Then, the display control unit 104 causes the display unit 105 to display an ultrasonic image in accordance with the ultrasonic image data.

The display unit 105 includes an LCD (liquid crystal display), a CRT (Cathode Ray tube), or any other type of display. The operational unit 106 includes a keyboard and a pointing device (not shown) or the like for allowing an operator to enter a command and information.

The control unit 107 includes a CPU (Central Processing Unit). This control unit 107 reads a control program stored in a memory unit which is not shown and causes respective components of the ultrasonic image display apparatus 100 to perform their functions.

Figure 3:
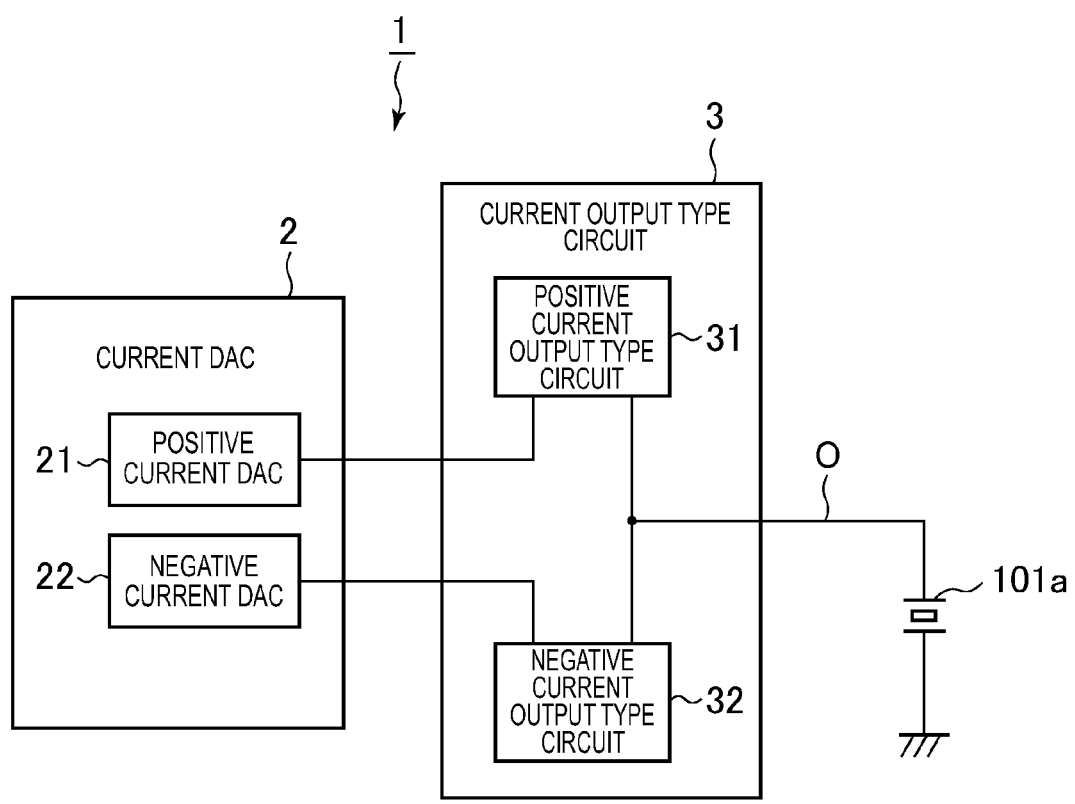
FIG. 3 is a diagram showing an outlined structure of an ultrasonic transducer driving circuit in the ultrasonic image display apparatus shown in FIG. 1.
Figure 4:
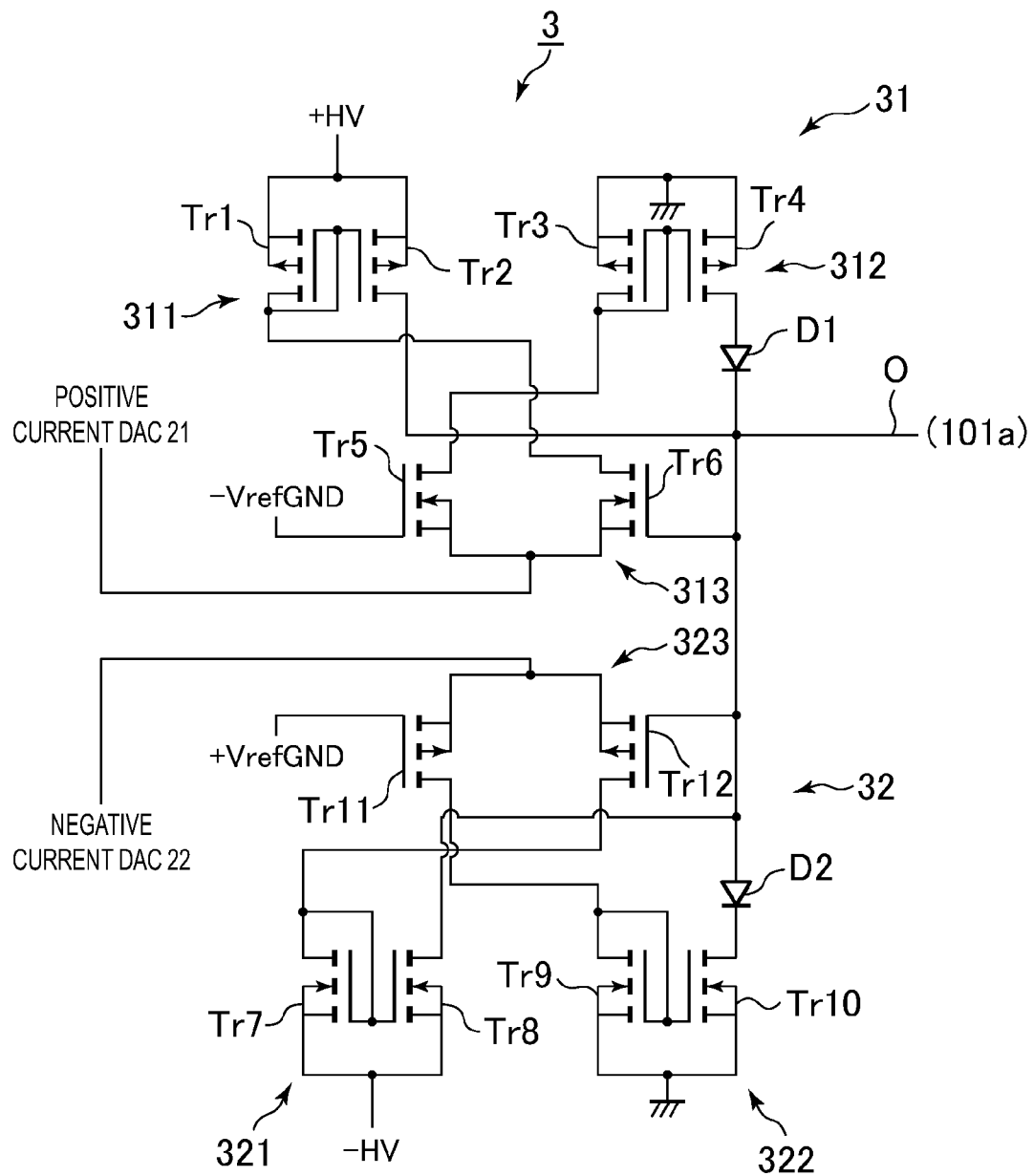
FIG. 4 is circuit diagram showing an ultrasonic transducer driving circuit in the ultrasonic image display apparatus shown in FIG. 1.

Description about the ultrasonic transducer driving circuits 1 is provided based on FIGS. 3 and 4. The number of the (plural) ultrasonic transducer driving circuits 1 corresponds to a maximum number of the ultrasonic transducers 101a which are used for transmission (only one of them is shown in FIG. 3). Each of the ultrasonic transducer driving circuits 1 includes a current DAC (Digital to Analog Converter) 2 and a current output type circuit 3. The current output type circuit 3 controls an output current flowing through an output line O and supplies electrical currents to the output line O for driving the corresponding ultrasonic transducer 101a. This output line O is one example of an embodiment of an output line.

In fact, the output line O is the output line of the current output type circuit 3 and also the output line of each of the ultrasonic transducer driving circuits 1. The output line of the current output type circuit 3 is the output line of each of the ultrasonic transducer driving circuits 1.

The current DAC 2 includes a positive current DAC 21 and a negative current DAC 22. The current output type circuit 3 includes a positive current output type circuit 31 and a negative current output type circuit 32. The current DAC 2 is one example of an embodiment of a current control. The current output type circuit 3 is one example of an embodiment of a current output type circuit.

The positive current DAC 21 and the negative current DAC 22 output a current for controlling an output current of the positive current output type circuit 31 and the negative current output type circuit 32.

The positive current DAC 21 is connected to the positive current output type circuit 31. The output current of the positive current output type circuit 31 is controlled by the current that is output from the positive current DAC 21 to the positive current output type circuit 31. The negative current DAC 22 is connected to the negative current output type circuit 32. The output current of the negative current output type circuit 32 is controlled by the current that is output from the negative current DAC 22 to the negative current output type circuit 32.

By the way, in conjunction with controlling the output currents of the positive current output type circuit 31 and the negative current output type circuit 32, the operations of a second current mirror circuit 312 and a fourth current mirror circuit 322 which will be described later are controlled. More specifically, the operations of the second current mirror circuit 312 and the fourth current mirror circuit 322 are controlled by the currents that are output from the positive current DAC 21 and the negative current DAC 22.

The positive current output type circuit 31 outputs a positive current to the corresponding ultrasonic transducer 101a. On the other hand, the negative current output type circuit 32 outputs a negative current to the corresponding ultrasonic transducer 101a.

How the positive current output type circuit 31 and the negative current output type circuit 32 are configured is described in detail based on FIG. 4. The positive current output type circuit 31 includes a first current mirror circuit 311, a second current mirror circuit 312, and a positive current switching circuit 313. The first current mirror circuit 311 is configured with a transistor Tr1 and a transistor Tr2. The second current mirror circuit 312 is configured with a transistor Tr3 and a transistor Tr4. The positive current switching circuit 313 is configured with a transistor Tr5 and a transistor Tr6. The transistors Tr1 to Tr4 are p-channel type MOSFETs (Metal-Oxide Semiconductor Field-Effect Transistors). The transistors Tr5, Tr6 are n-channel type MOSFETs.

The operations of the first current mirror circuit 311 and the second current mirror circuit 312 are controlled by the output current of the positive current DAC 21, as will be described later. The first current mirror circuit 311 is one example of an embodiment of a positive current mirror circuit. The second current mirror circuit 312 is one example of an embodiment of a second current discharge circuit.

For the transistors Tr1, Tr2, their gate terminals are connected to each other and their source terminals are connected to a power supply voltage +HV. A drain terminal of the transistor Tr1 is connected to a drain terminal of the transistor Tr6 and a drain terminal of the transistor Tr2 is connected to the output line O.

For the transistors Tr3, Tr4, their gate terminals are connected to each other and their source terminals are connected to a ground. A drain terminal of the transistor Tr3 is connected to the transistor Tr5 and a drain terminal of the transistor Tr4 is connected to the output line O. Besides, a diode D1 is connected between a drain terminal of the transistor Tr4 and the output line O. This diode D1 is connected, oriented so that a current flows from the transistor Tr4 toward the output line O.

For the transistors Tr5, Tr6, their source terminals are connected to the positive current DAC 21. A gate terminal of the transistor Tr5 is connected to a voltage −VrefGND and a gate terminal of the transistor Tr6 is connected to the output line O. By the way, −VrefGND is a voltage that is lower by a predetermined voltage than ground.

The positive current switching circuit 313 formed of the transistors Tr5, Tr6 is a differential amplifier circuit in which the transistor Tr6 will be OFF when the transistor Tr5 is put in an ON state, whereas the transistor Tr6 will be ON when the transistor Tr5 is put in an OFF state. The transistor Tr6 is put in an ON state when the output line O is at a positive voltage and in an OFF state when the output line O is at a negative voltage. Hence, the transistor Tr5 is put in an OFF state when the output line O is at a positive voltage and in an ON state when the output line O is at a negative voltage.

The negative current output circuit 32 includes a third current mirror circuit 321, a fourth current mirror circuit 322, and a negative current switching circuit 323. The third current mirror circuit 321 is configured with a transistor Tr7 and a transistor Tr8. The fourth current mirror circuit 322 is configured with a transistor Tr9 and a transistor Tr10. The negative current switching circuit 323 is configured with a transistor Tr11 and a transistor Tr12. The transistors Tr7 to Tr10 are n-channel type MOSFETs (Metal-Oxide Semiconductor Field-Effect Transistors). The transistors Tr11, Tr12 are p-channel type MOSFETs.

The third current mirror circuit 321 is one example of an embodiment of a negative current mirror circuit. The fourth current mirror circuit 322 is one example of an embodiment of a first current discharge circuit.

For the transistors Tr7, Tr8, their gate terminals are connected to each other and their source terminals are connected to a power supply voltage −HV. A drain terminal of the transistor Tr7 is connected to a drain terminal of the transistor Tr12 and a drain terminal of the transistor Tr8 is connected to the output line O.

For the transistors Tr9, Tr10, their gate terminals are connected to each other and their source terminals are connected to a ground. A drain terminal of the transistor Tr9 is connected to the transistor Tr11 and a drain terminal of the transistor Tr10 is connected to the output line O. Besides, a diode D2 is connected between the drain terminal of the transistor Tr10 and the output line O. This diode D2 is connected to be oriented so that a current flows from the output line O toward the transistor Tr10.

For the transistors Tr11, Tr12, their source terminals are connected to the negative current DAC 22. A gate terminal of the transistor Tr11 is connected to a voltage +VrefGND and a gate terminal of the transistor Tr12 is connected to the output line O. By the way, +VrefGND is a voltage that is higher by a predetermined voltage than ground.

The negative current switching circuit 323 formed of the transistors Tr11, Tr12 is a differential amplifier circuit in which the transistor Tr12 will be OFF when the transistor Tr11 is put in an ON state, whereas the transistor Tr12 will be ON when the transistor Tr11 is put in an OFF state. The transistor Tr12 is put in an OFF state when the output line O is at a positive voltage and in an ON state when the output line O is at a negative voltage. Hence, the transistor Tr11 is put in an ON state when the output line O is at a positive voltage and in an OFF state when the output line O is at a negative voltage.

Then, how an ultrasonic transducer driving circuit 1 of the present example operates is described. In this ultrasonic transducer driving circuit 1, a positive current is output from the positive current output type circuit 31 and a negative current is output from the negative current output type circuit 32 and electrical currents for driving the corresponding ultrasonic transducer 101a are output. This is explained specifically below.

Figure 5:
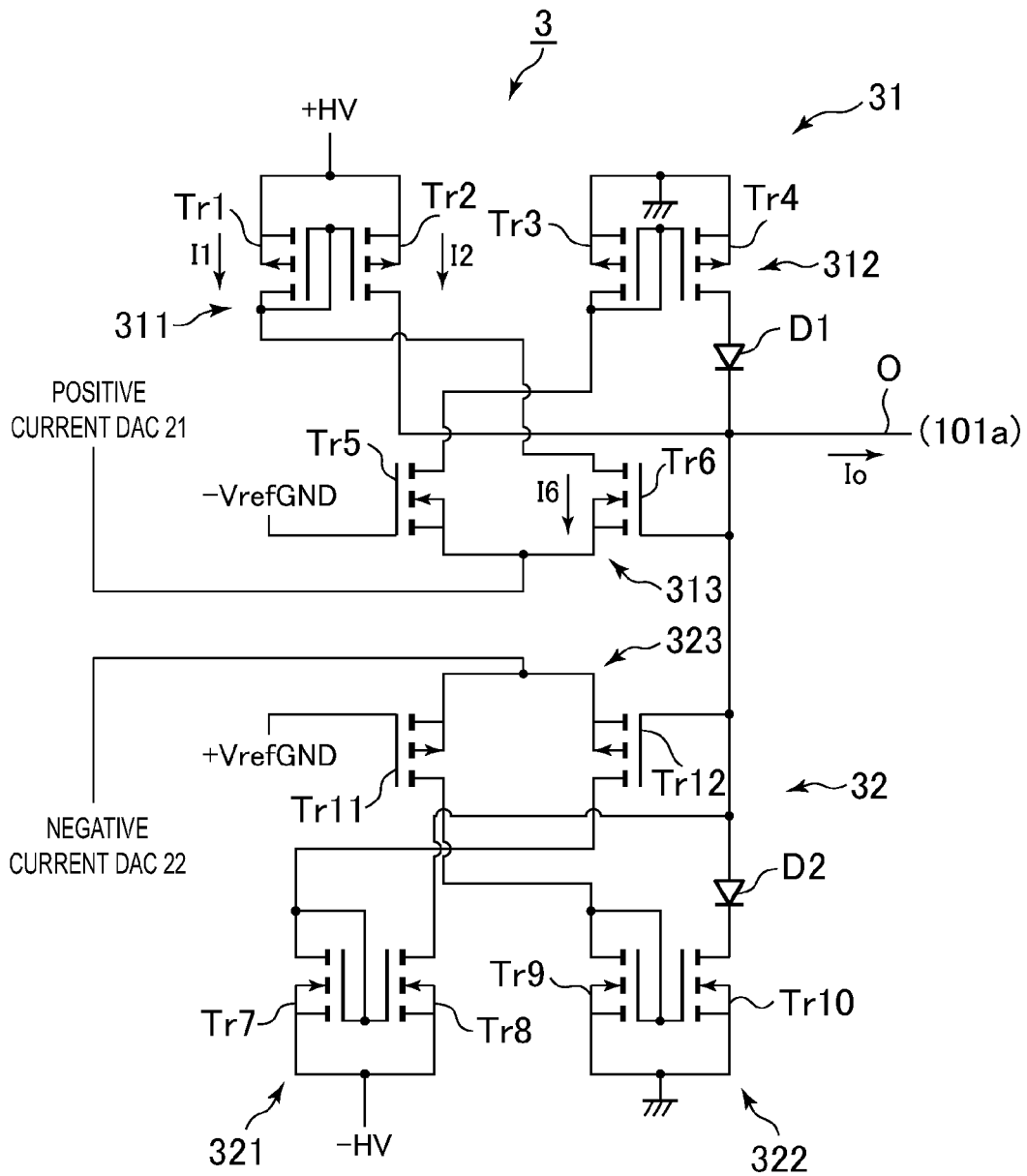
FIG. 5 is a diagram for explaining how a first current mirror circuit operates.

First, the first current mirror circuit 311 operates and a positive current +Io is output. Concretely speaking, as shown in FIG. 5, a negative current −Ii is input from the positive current DAC 21 to the positive current output type circuit 31. At this time, the transistor Tr6 is put in an ON state and there is a current I6 flowing through this transistor Tr6. This, in consequence, produces a current I1 flowing through the transistor Tr1 and a current I2 flowing through the transistor Tr2. This current I2 is output to the output line O as the positive current +Io and the voltage of this output line O rises and becomes a positive voltage.

Figure 6:
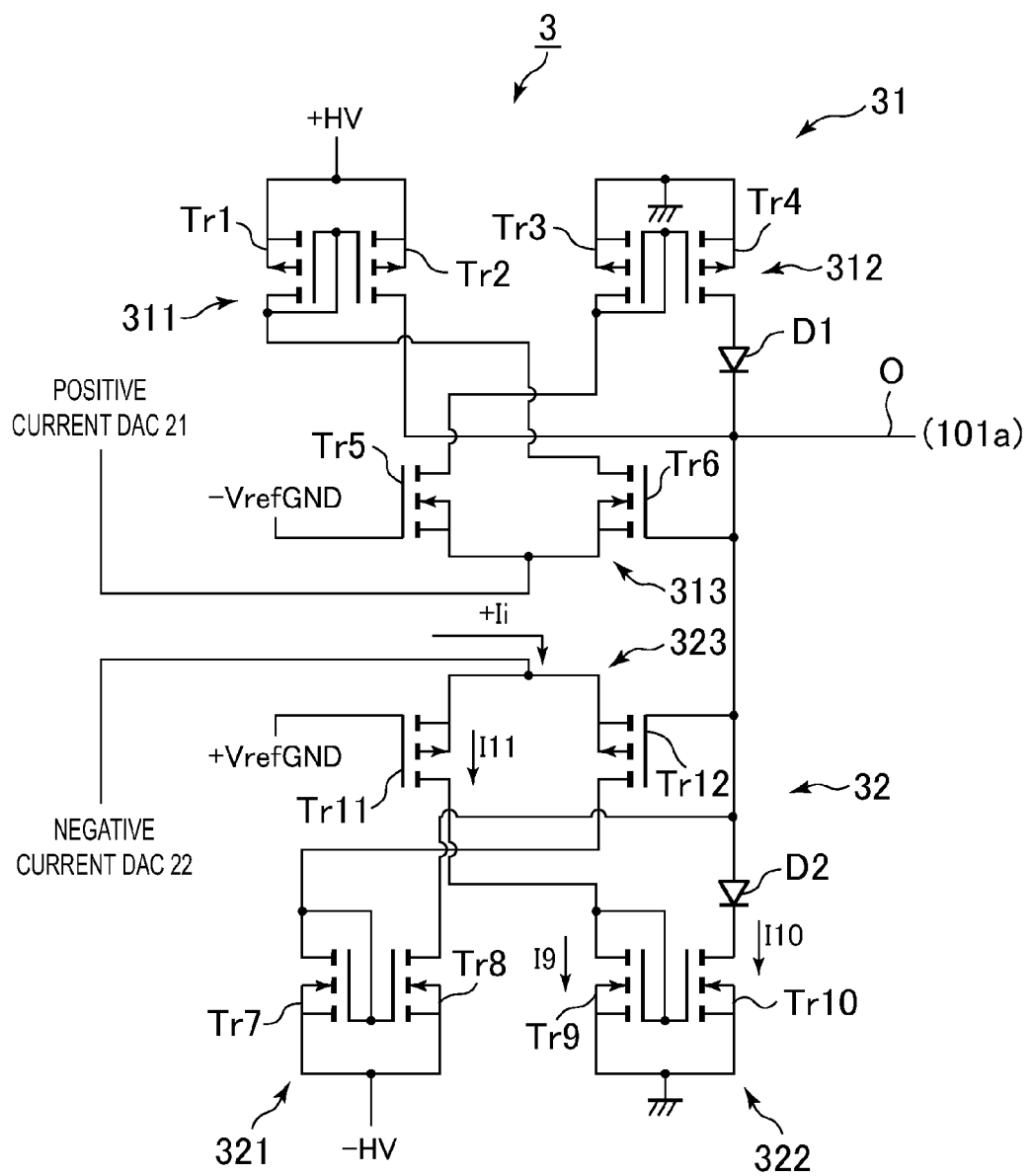
FIG. 6 is a diagram for explaining how a fourth current mirror circuit operates.

Then, the fourth current mirror circuit 322 operates and the output of the positive current +Io causes discharging of electric charges accumulated in the ultrasonic transducer 101a. Concretely, as shown in FIG. 6, instead of the input of the negative current −Ii from the positive current DAC 21 to the positive current output type circuit 31, a positive current +Ii is input from the negative current DAC 22 to the negative current output type circuit 32. At this time, the transistor Tr11 is put in an ON state and, therefore, the positive current +Ii produces a current I11 flowing through the transistor Tr11, a current I9 flowing through the transistor Tr9, and a current I10 flowing through the transistor Tr10. This current I10 is a current arising from electric charges accumulated in the ultrasonic transducer 101a and is one example of an embodiment of a current flowing from the output line to ground.

Figure 7:
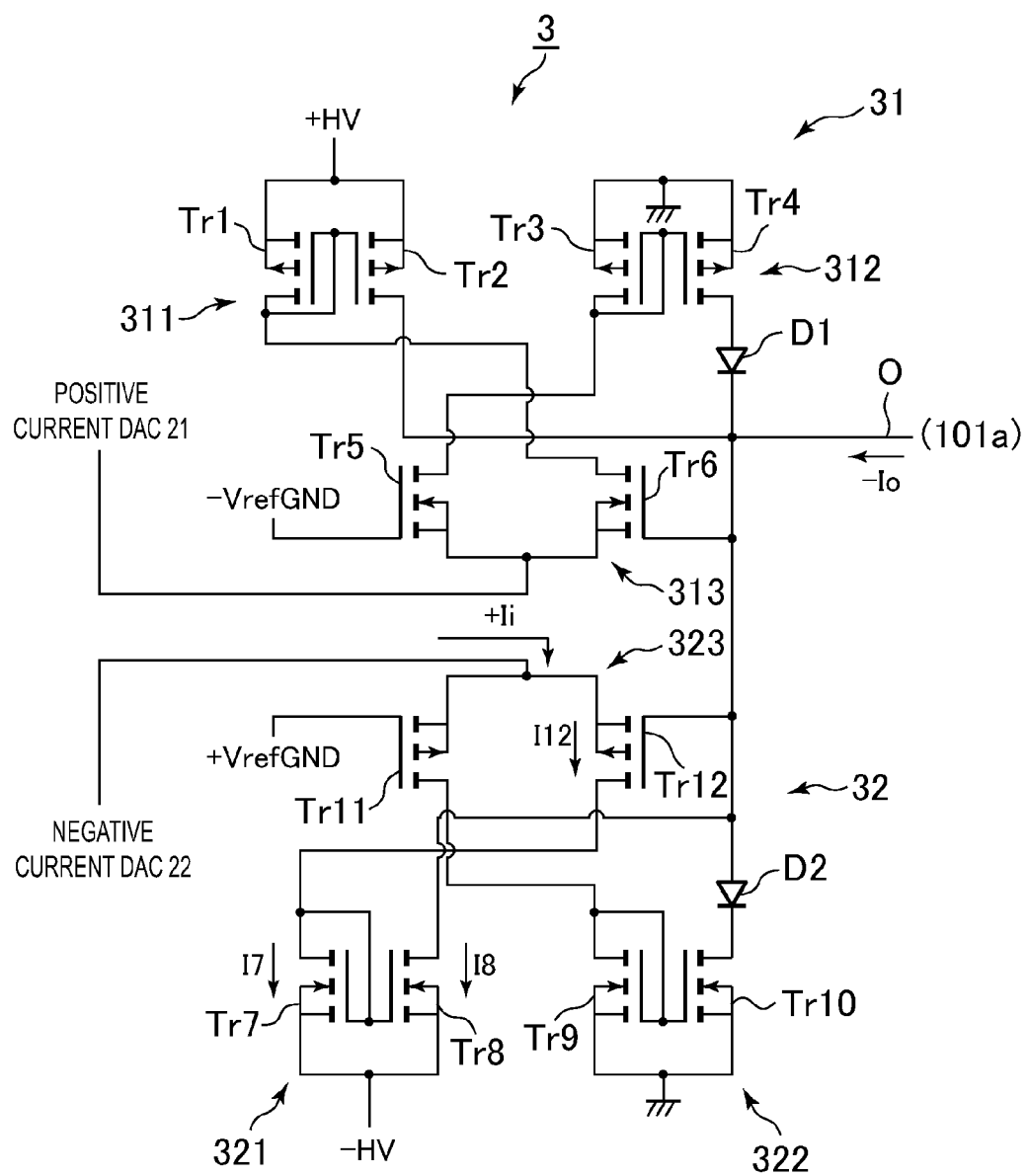
FIG. 7 is a diagram for explaining how a third current mirror circuit operates.

In turn, the third current mirror circuit 321 operates. Concretely, the flowing of the current I10 causes a decrease in the voltage (positive voltage) of the output line O. Then, when the voltage of the output line O comes to the voltage +VrefGND, the transistor Tr12 turns into an ON state, whereas the transistor Tr11 turns into an OFF state. As shown in FIG. 7, the turning of the transistor Tr12 into the ON state produces a current I12 flowing through this transistor Tr12. This, in consequence, produces a current I7 flowing through the transistor Tr7 and a current I8 flowing through the transistor Tr8. This current I8 is output to the output line O as a negative current −Io and the voltage of this output line O falls and becomes a negative voltage.

Figure 8:
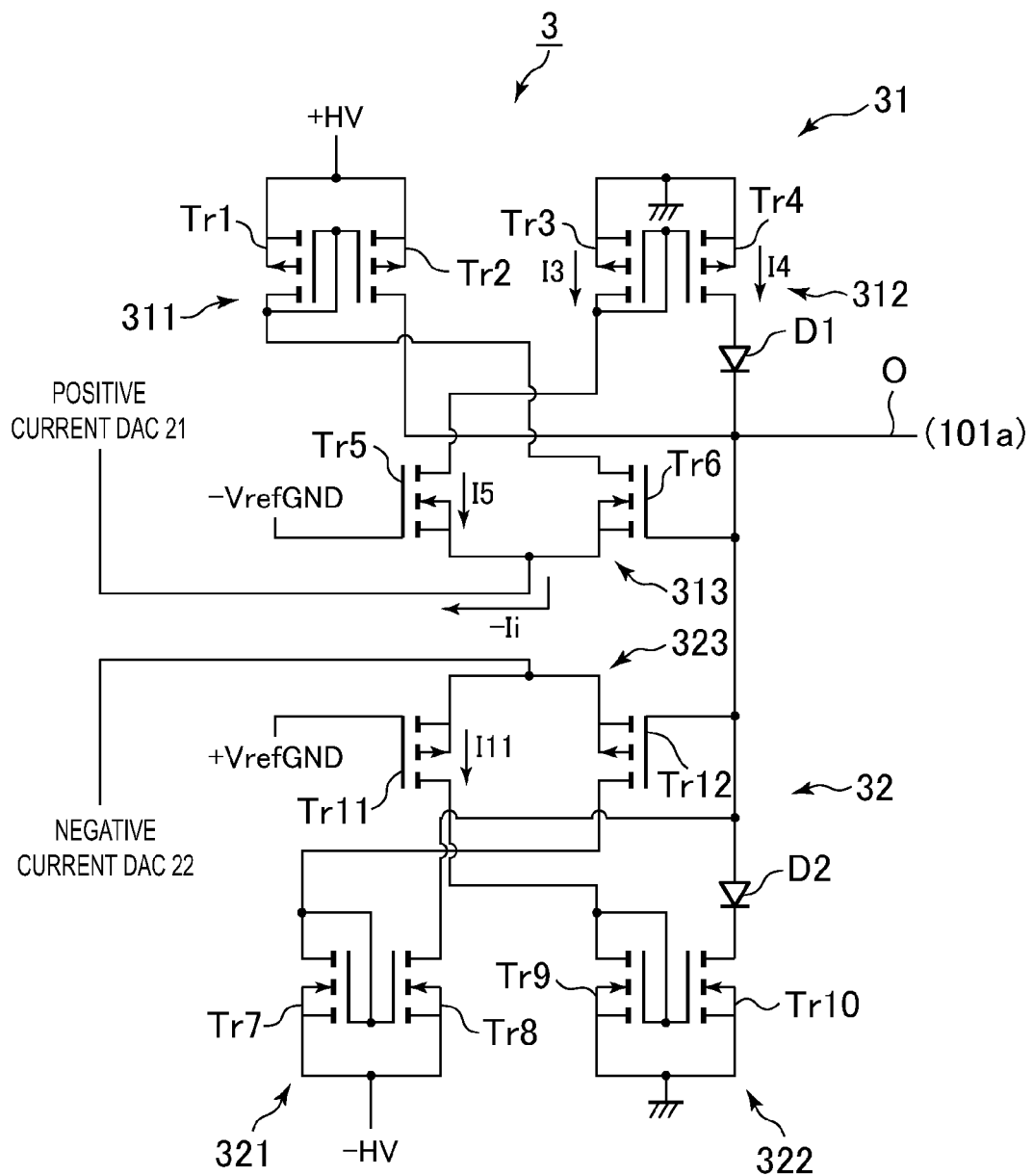
FIG. 8 is a diagram for explaining how a second current mirror circuit operates.
Figure 9:
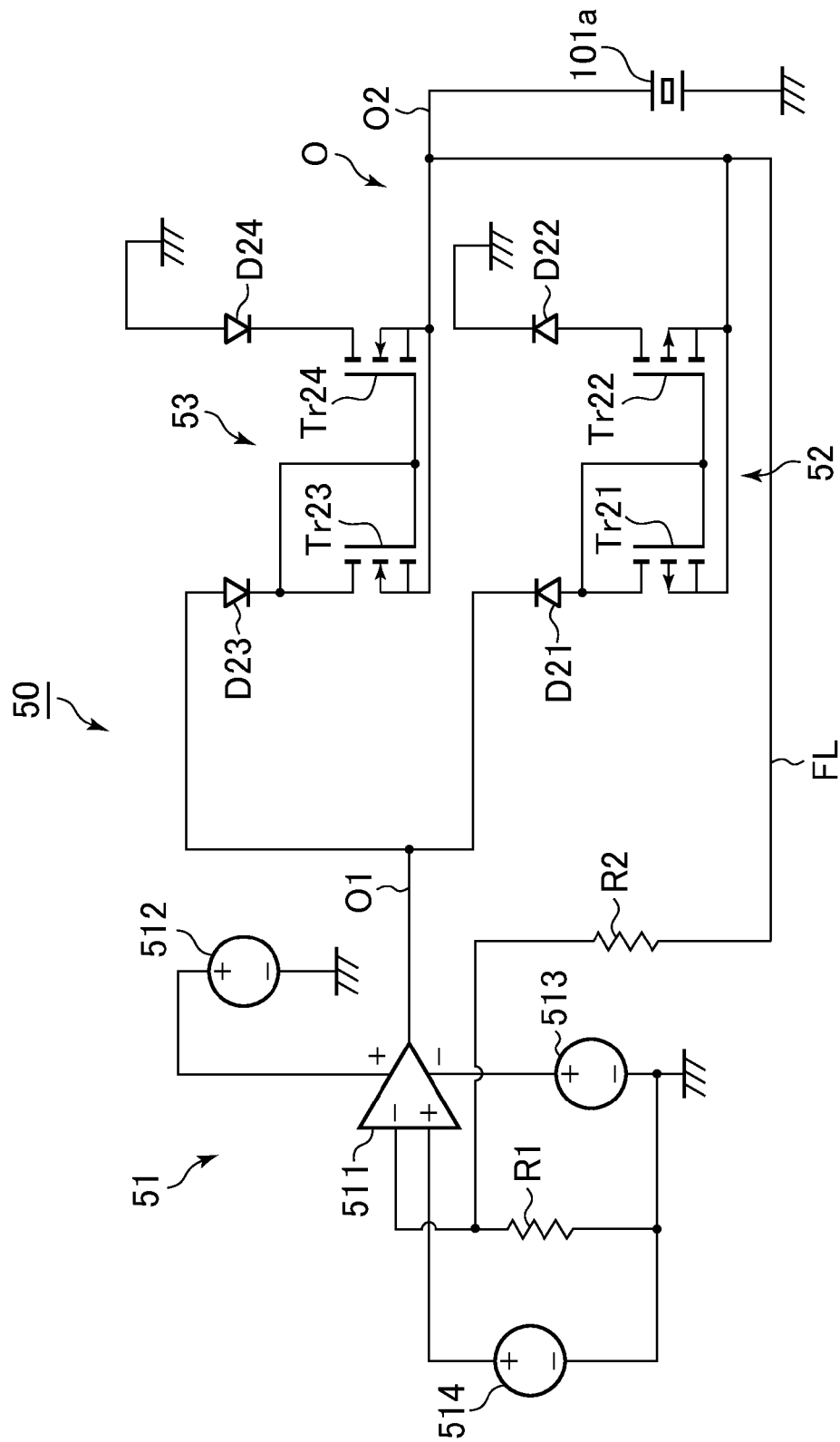
FIG. 9 is a circuit diagram showing an ultrasonic transducer driving circuit of a second embodiment.

Then, the second current mirror circuit 312 operates and the output of the negative current −Io causes discharging of electric charges accumulated in the ultrasonic transducer 101a. Concretely, as shown in FIG. 8, instead of the input of the positive current +Ii from the negative current DAC 22 to the negative current output type circuit 32, the negative current −Ii is input from the positive current DAC 21 to the positive current output type circuit 31. At this time, the transistor Tr5 is put in an ON state and, therefore, the negative current −Ii produces a current I5 flowing through the transistor Tr5, a current I3 flowing through the transistor Tr3, and a current I4 flowing through the transistor Tr4. This current I4 is a current arising from electric charges accumulated in the ultrasonic transducer 101a and is one example of an embodiment of a current flowing from ground to the output line.

The flowing of the current I4 causes an increase of the voltage (negative voltage) of the output line O. Then, when the voltage of the output line O comes to the voltage −Vref-GND, the transistor Tr6 turns into an ON state, whereas the transistor Tr5 turns into an OFF state. The turning of the transistor Tr6 into the ON state produces the current I2 again and the positive current +Io is supplied to the output line O.

According to the ultrasonic transducer driving circuit 1 of the present example, when the output line O is at a positive voltage, the current arising from electric charges accumulated in the ultrasonic transducer 101a flows from the output line O to ground via the fourth current mirror circuit 322. Likewise, when the output line O is at a negative voltage, the current arising from electric charges accumulated in the ultrasonic transducer 101a flows from ground to the output line O via the second current mirror circuit 312. In this way, the current arising from electric charges accumulated in the ultrasonic transducer 101a does not flow through the first current mirror circuit 311 and the third current mirror circuit 321 and, thus, power consumption can be reduced.

Second Embodiment

Next, a second embodiment is described. Ultrasonic transducer driving circuits 50 of the present example are provided in the transmitter unit 1021 of the ultrasonic image display apparatus 100 (see FIG. 1 and FIG. 2), as is the case for the ultrasonic transducer driving circuits 1 of the first embodiment.

As shown in FIG. 8, each of the ultrasonic transducer driving circuits 50 includes a voltage output type circuit 51, a first current discharge circuit 52, and a second current discharge circuit 53. The voltage output type circuit 51 controls an output voltage of an output line O and supplies an electrical current to an output line O for driving the corresponding ultrasonic transducer 101a. This output line O is one example of an embodiment of an output line.

The output line O is the output line of the voltage output type circuit 51 and also the output line of each of the ultrasonic transducer driving circuits 1. The output line of the voltage output type circuit 51 is the output line of each of the ultrasonic transducer driving circuits 50.

Figure 10:
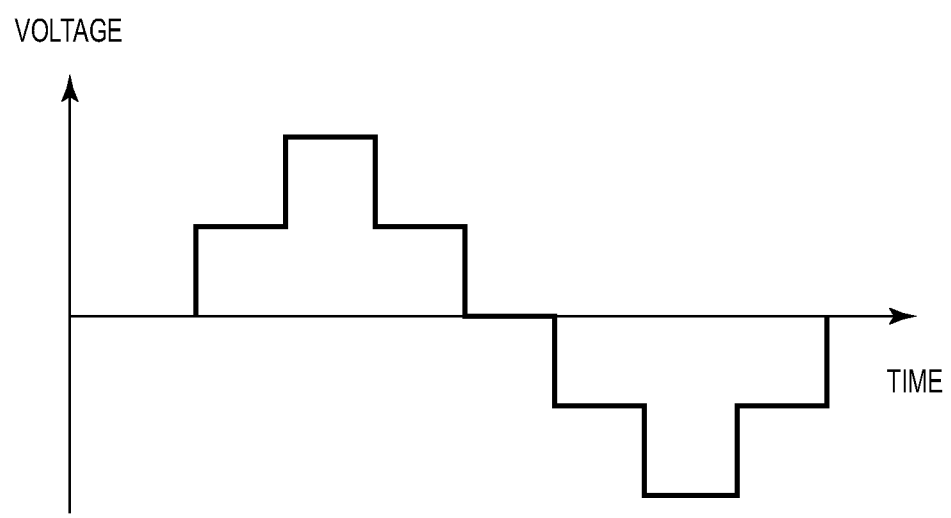
FIG. 10 is a diagram showing a voltage waveform with five levels of voltages.

The voltage output type circuit 51 is a multi-level pulser having three or more levels of output voltages. For example, the voltage output type circuit 51 outputs five levels of voltages as output voltages, as is illustrated in FIG. 10. This is, however, not to be regarded as limiting.

The voltage output type circuit 51 includes an operational amplifier 511. To this operational amplifier 511, a positive power supply 512 which supplies a positive supply voltage and a negative power supply 513 which supplies a negative supply voltage are connected.

Besides, a power supply 514 is connected to a non-inverting input terminal (+) of the operational amplifier 511. On end of this power supply 514 is connected to the non-inverting input terminal (+) and the other end is connected to a ground.

A resistor R1 is connected between an inverting input terminal (−) of the operational amplifier 511 and the ground. The other end of a feedback line FL whose one end is connected to the output line O and having a resistor R2 is connected between this resistor R1 and the inverting input terminal (−). Thus, by way of this feedback line FL, the output voltage of the output line O is divided by the resistor R2 and input to the inverting input terminal (−).

The first current discharge circuit 52 and the second current discharge circuit 53 are provided along the output line O. In other words, the first current discharge circuit 52 and the second current discharge circuit 53 are provided between the voltage output type circuit 51 and the corresponding ultrasonic transducer 101a. The first current discharge circuit 52 is configured with a current mirror circuit having transistors Tr21 and Tr22. The second current discharge circuit 53 is configured with a current mirror circuit having transistors Tr23 and Tr24. The transistors Tr21 and Tr22 are p-channel type MOSFETs and the transistors Tr23 and Tr24 are n-channel type MOSFETs.

For the transistors Tr21 and Tr22, their gate terminals are connected to each other and their source terminals are connected to the ultrasonic transducer 101a. A drain terminal of the transistor Tr21 is connected to the voltage output type circuit 51 and a drain terminal of the transistor Tr22 is connected to the ground.

For the transistors Tr23, Tr24, their gate terminals are connected to each other and their source terminals are connected to the ultrasonic transducer 101a. A drain terminal of the transistor Tr23 is connected to the voltage output type circuit 51 and a drain terminal of the transistor Tr24 is connected to the ground.

Here, a path between the transistors T21, T22 and an output terminal of the operational amplifier 511 is assumed as a first output line O1. A path between the transistors Tr21 to Tr24 and the ultrasonic transducer 101a is assumed as a second output line O2. That is, the output line includes the first output line O1 and the second output line O2. One end of the first output line O1 is connected to the output terminal of the operational amplifier 511 and the other end branches to connect to the drain terminals of the transistors Tr21 and Tr23.

The operations of the first current discharge circuit 52 and the second current discharge circuit 53 are controlled according to an output voltage of the voltage output type circuit 51. In the present example, the operations of the first current discharge circuit 52 and the second current discharge circuit 53 are controlled by the voltage difference between the second output line O2 and the first output line O1. Further details will be provided later.

Diodes D21 and D23 are connected at points on the branches of the first output line O1. The diode D21 is connected to be oriented so that a current flows from the transistor Tr21 toward the output terminal of the operational amplifier 511. The diode D23 is connected to be oriented so that a current flows from the output terminal of the operational amplifier 511 toward the transistor Tr23.

However, the diodes D21 and D23 may not necessarily be provided.

A diode D22 is connected between the transistor Tr22 and the ground. A diode D24 is connected between the transistor Tr24 and the ground. The diode D22 is connected to be oriented so that a current flows from the transistor Tr22 toward the ground. The diode D24 is connected to be oriented so that a current flows from the ground toward the transistor Tr24.

Figure 11:
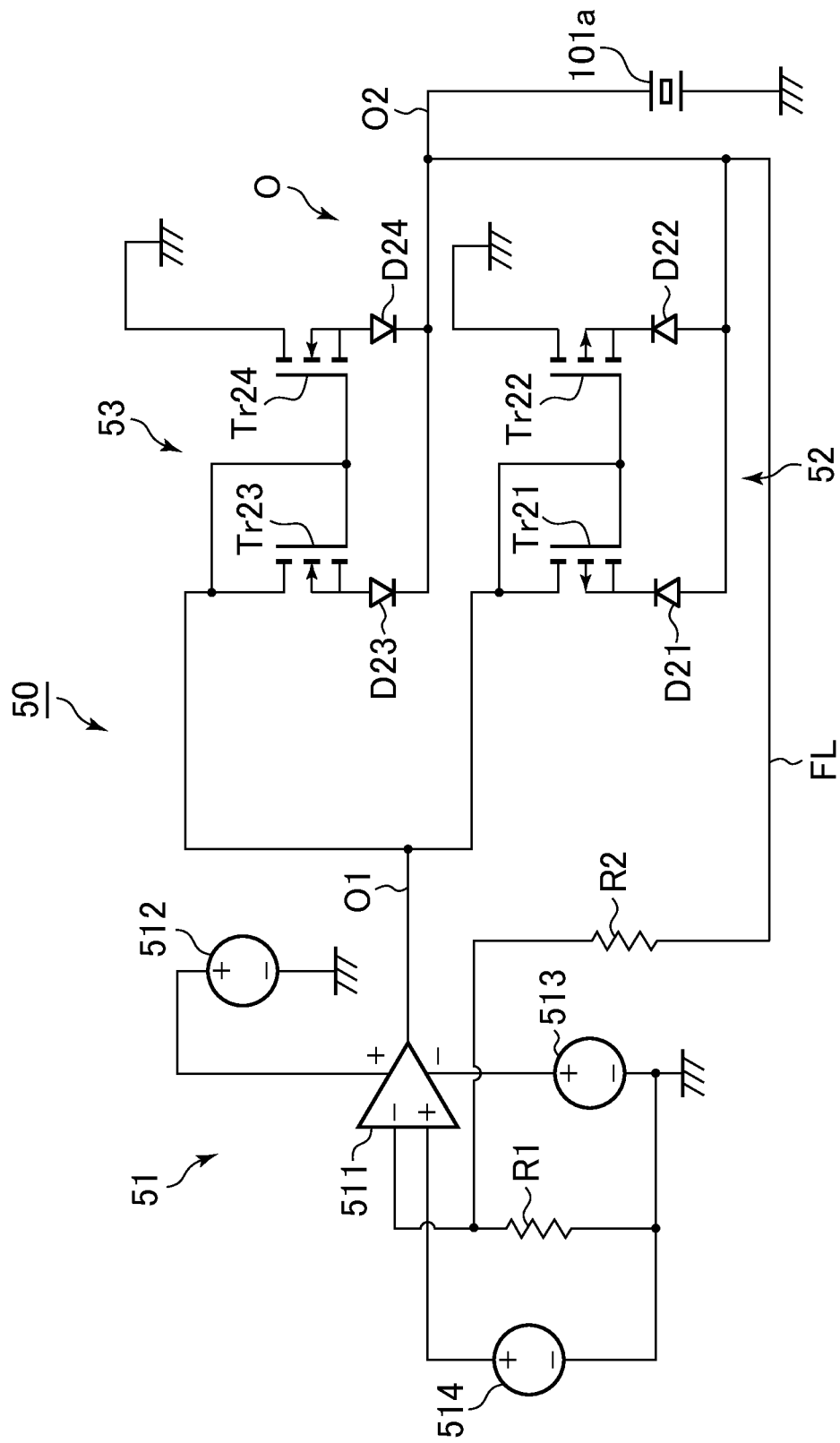
FIG. 11 is a circuit diagram showing another example of an ultrasonic transducer driving circuit of the second embodiment.

Here, as shown in FIG. 11, the diode D21 may be connected between the source terminal of the transistor Tr21 and the second output line O2. The diode D22 may be connected between the source terminal of the transistor Tr22 and the second output line O2. The diode D23 may be connected between the transistor Tr23 and the second output line O2. The diode D24 may be connected between the transistor Tr24 and the second output line O2.

Although not shown particularly, an additional circuit may be provided to avoid an excessive inverse voltage between the gate and source terminals of the transistors Tr21 to Tr24.

Figure 12:
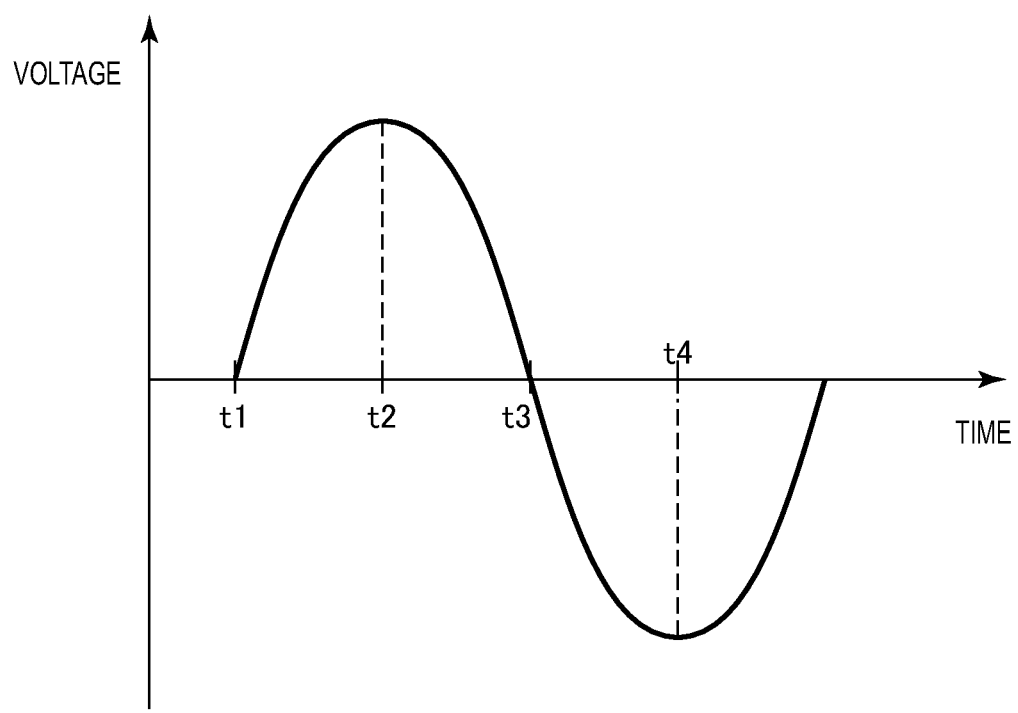
FIG. 12 is a diagram showing one example of a waveform of an output voltage that is output from a voltage output type circuit.

Then, how an ultrasonic transducer driving circuit 1 of the present example operates is described. In this ultrasonic transducer driving circuit 1, a voltage having a waveform that is shown in FIG. 12 is output from the voltage output type circuit 51. In FIG. 12, the waveform of an output voltage is simplified and represented as a sine wave.

Figure 13:
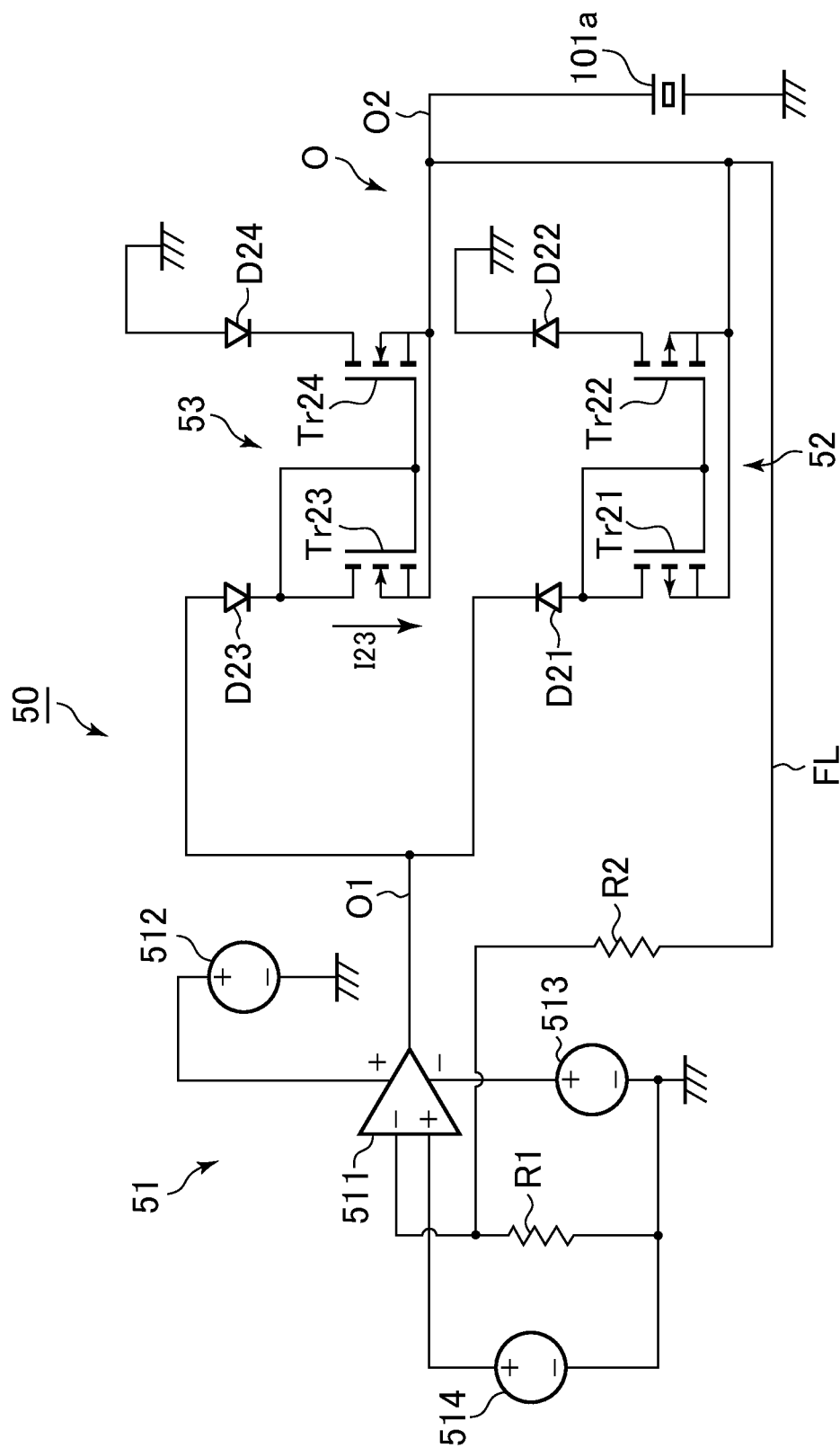
FIG. 13 is a diagram for explaining how the ultrasonic transducer driving circuit of the second embodiment operates.

In a state in which the second output line O2 is at a ground voltage, when an output voltage starts to be supplied from the voltage output type circuit 51 to the first output line O1 at time t1, the voltage of this first output line O1 rises and the output voltage becomes a positive voltage. This produces a current I23 flowing through the transistor Tr23, as shown in FIG. 13, and the voltage of the second output line O2 rises.

Figure 14:
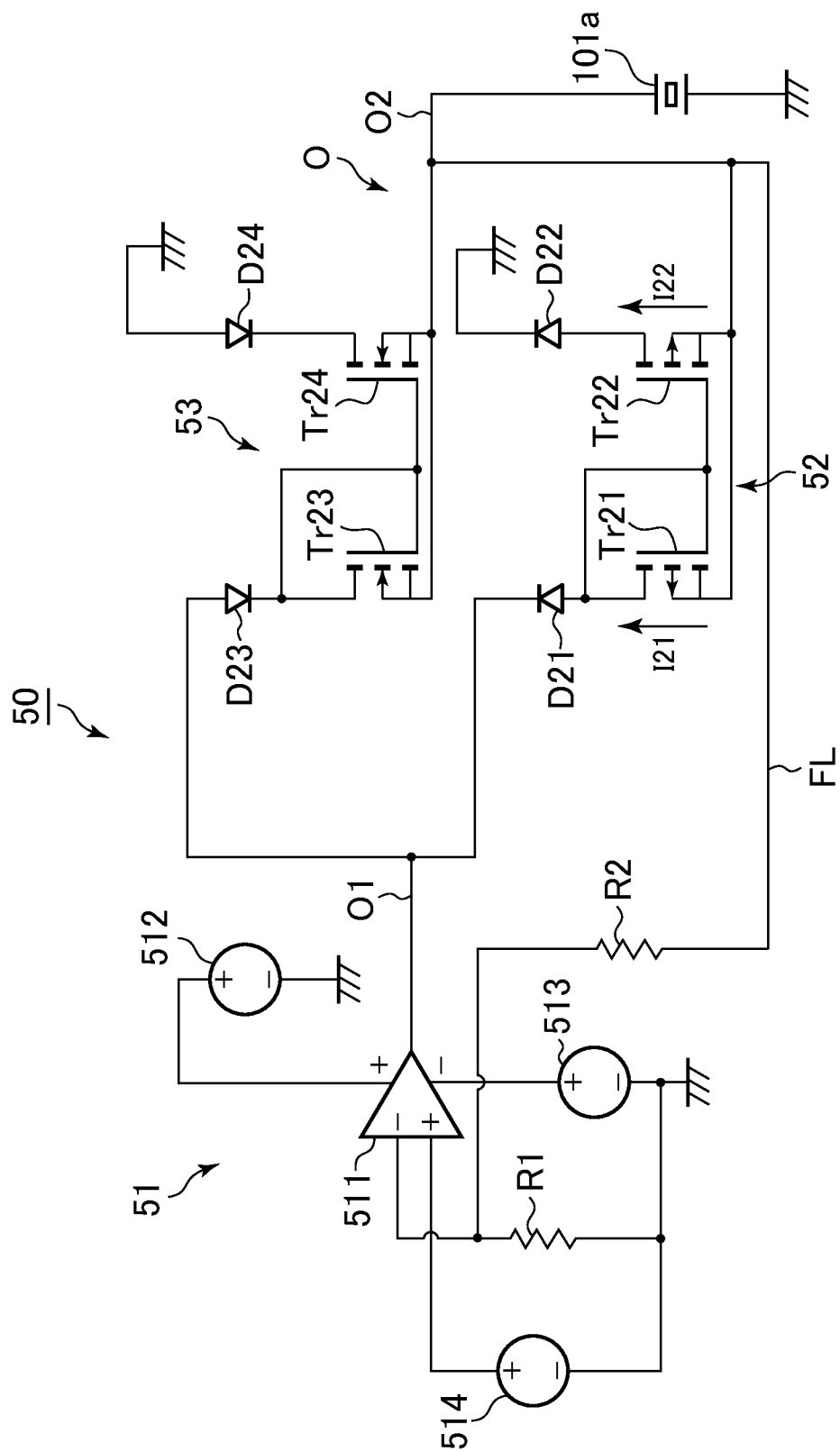
FIG. 14 is a diagram for explaining how the ultrasonic transducer driving circuit of the second embodiment operates.

Then, after the output voltage of the voltage output type circuit 51 has reached a peak at time t2, when it starts to fall, the voltage of the second output line O2 becomes smaller than that of the first output line O1, thereby producing a current I21 flowing through the transistor Tr21 and a current I22 flowing through the transistor Tr22, as shown in FIG. 14. The current I21 is a current that flows from the second output line O2 toward the first output line O1. The current I22 is a current that flows from the second output line O2 toward the ground.

Figure 15:
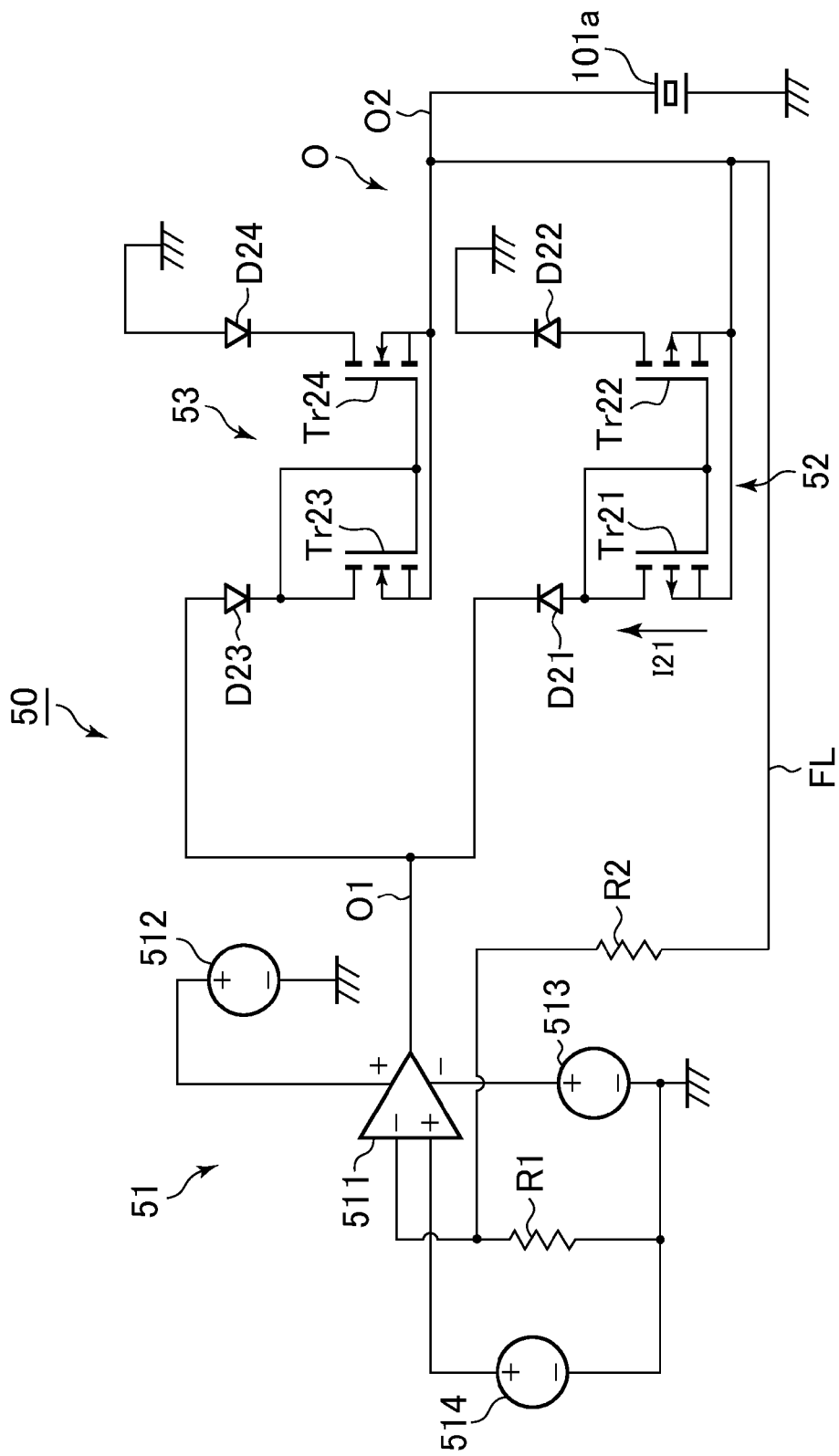
FIG. 15 is a diagram for explaining how the ultrasonic transducer driving circuit of the second embodiment operates.

Then, after the output voltage of the voltage output type circuit 51 has become equal to the ground voltage at time t3, when it further falls and becomes a negative voltage, the second output line O2 becomes lower than the ground voltage, thus resulting in that the current I21 only flows, but the current I22 does not flow, as shown FIG. 15.

Figure 16:
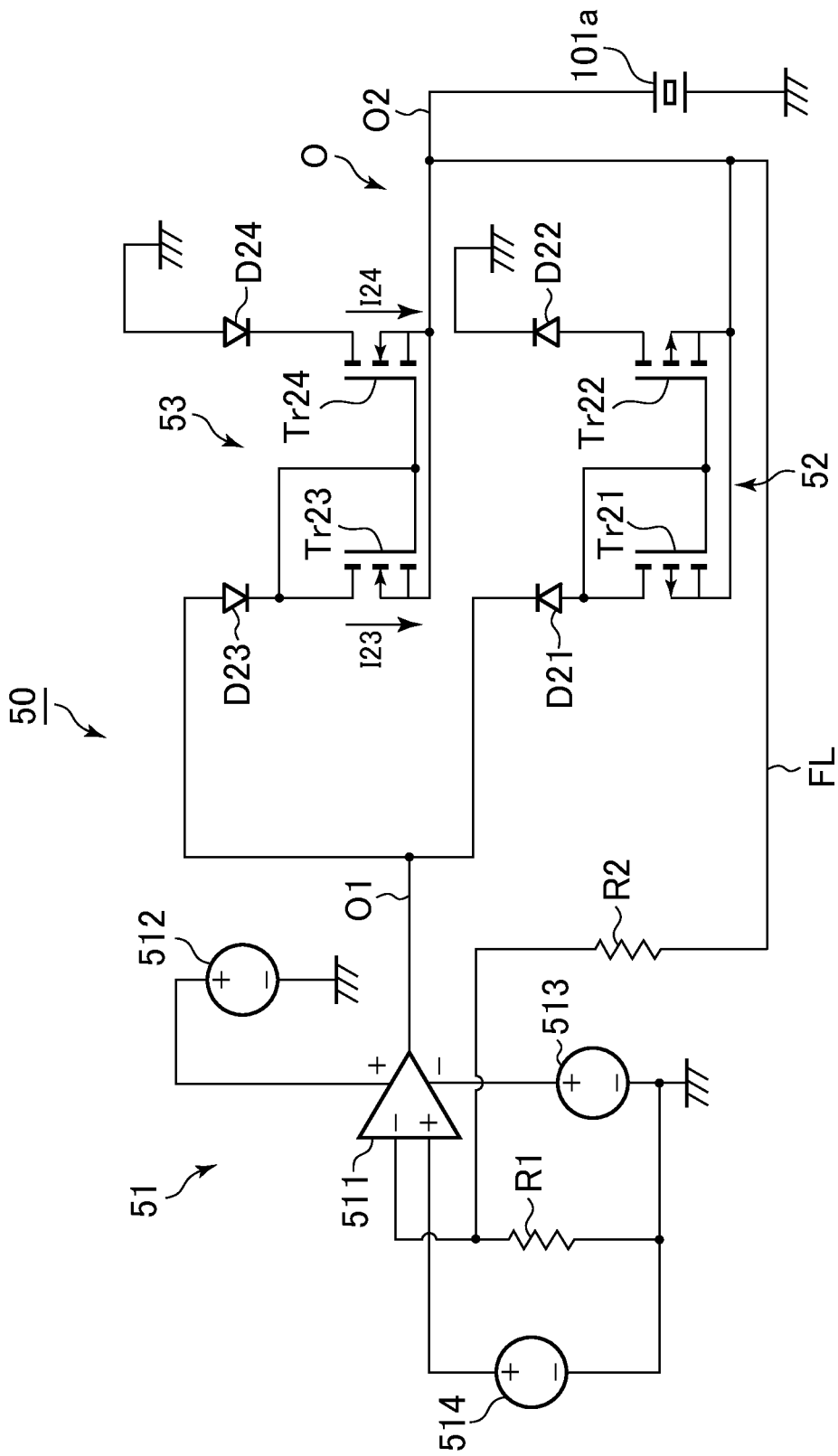
FIG. 16 is a diagram for explaining how the ultrasonic transducer driving circuit of the second embodiment operates.

Then, after the output voltage of the voltage output type circuit 51 has become minimum, when it starts to rise, the voltage of the first output line O1 becomes larger than that of the second output line O2, thereby producing a current I23 flowing through the transistor Tr23 and a current I24 flowing through the transistor Tr24, as shown in FIG. 16. The current I23 is a current that flows from the first output line O1 toward the second output line O2. The current I23 is a current that flows from the ground toward the second output line O2.

According to the ultrasonic transducer driving circuits 50 of the present example, when the output line O is at a positive voltage, the current arising from electric charges accumulated in the ultrasonic transducer 101a flows from the second output line O2 to the ground as the current I22 via the first current discharge circuit 52 and also flows from the second output line O2 to the first output line O1 as the current I21. Therefore, power consumption can be reduced by an amount equivalent to the amount of the current I22 flowing.

Likewise, when the output line O is at a negative voltage, the current arising from electric charges accumulated in the ultrasonic transducer 101a flows from the ground to the second output line O2 as the current I24 via the second current discharge circuit 53 and also flows from the first output line O1 to the second output line O2 as the current I23. Therefore, power consumption can be reduced by an amount equivalent to the amount of the current I24 flowing.

Figure 17:
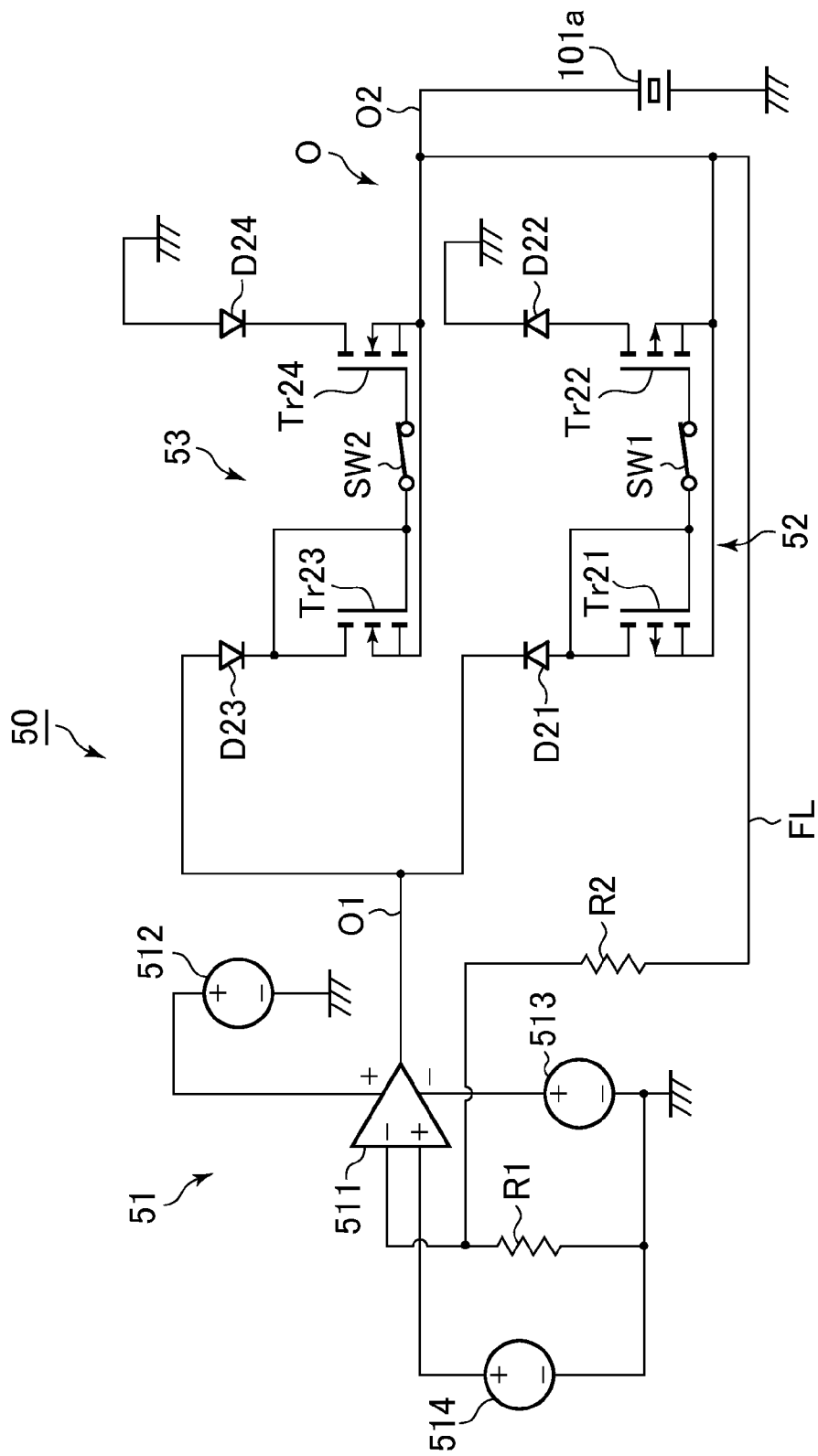
FIG. 17 is a circuit diagram showing an ultrasonic transducer driving circuit of a first example of modification to the second embodiment.
Figure 18:
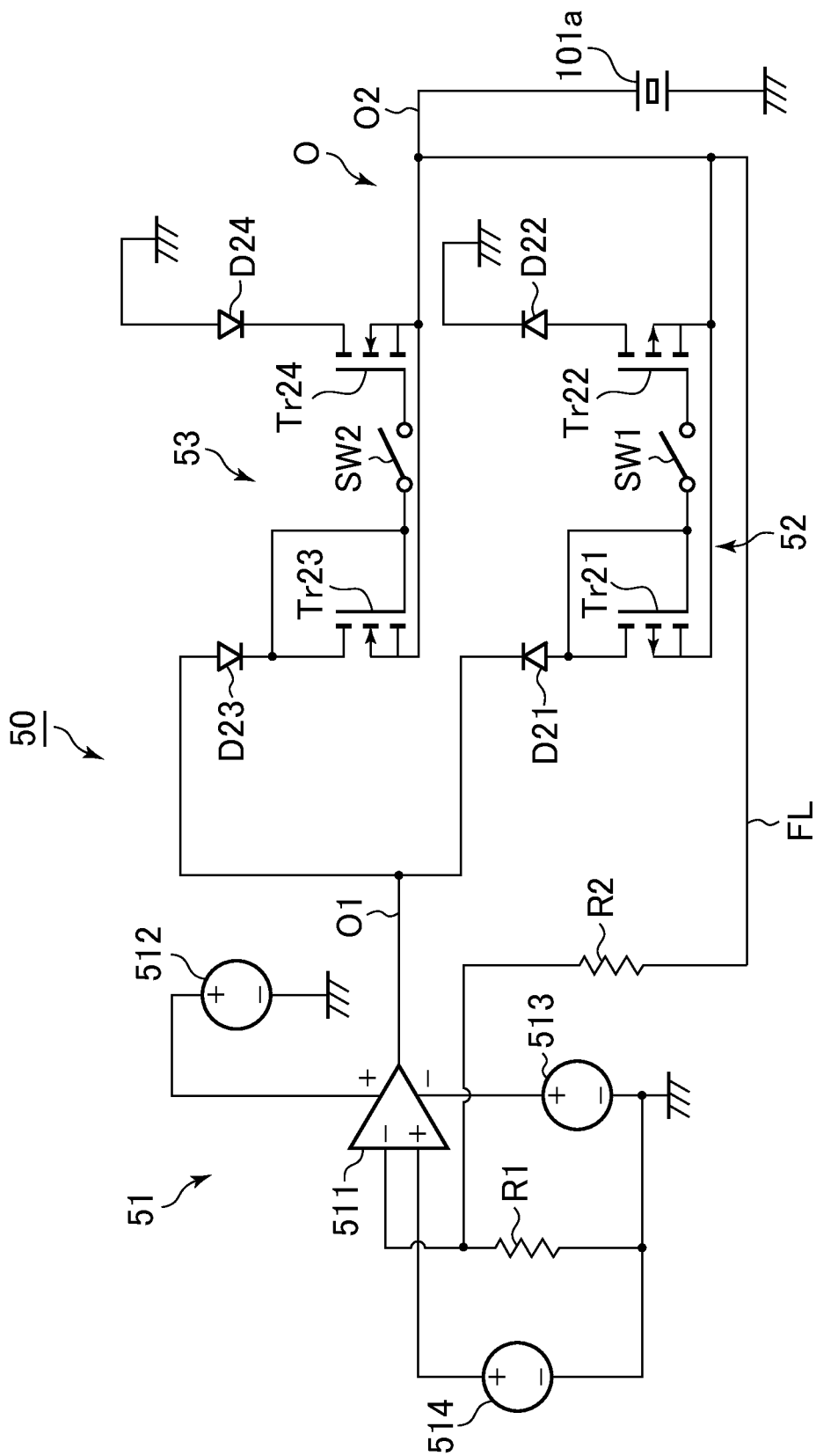
FIG. 18 is a circuit diagram in which switches were turned off in the ultrasonic transducer driving circuit shown in FIG. 17.

Next, examples of modification to the second embodiment are described. To being with, a first modification example is described. In an ultrasonic transducer driving circuit 50 of the first modification example, a switch SW1 is provided on a connection path between the transistors Tr21 and Tr22, that is, between the gate terminals of the transistors Tr21 and Tr22, as shown in FIG. 17. Besides, a switch SW2 is provided on a connection path between the transistors Tr23 and Tr24, that is, between the gate terminals of the transistors Tr23 and Tr24. As shown in FIG. 18, by turning the switches SW1 and SW2 off, it is possible to make the transistors Tr22 and Tr24 and the diodes D22 and D24 operate as a ground clamp circuit that keeps the voltage of the output line O at the ground voltage level.

Figure 19:
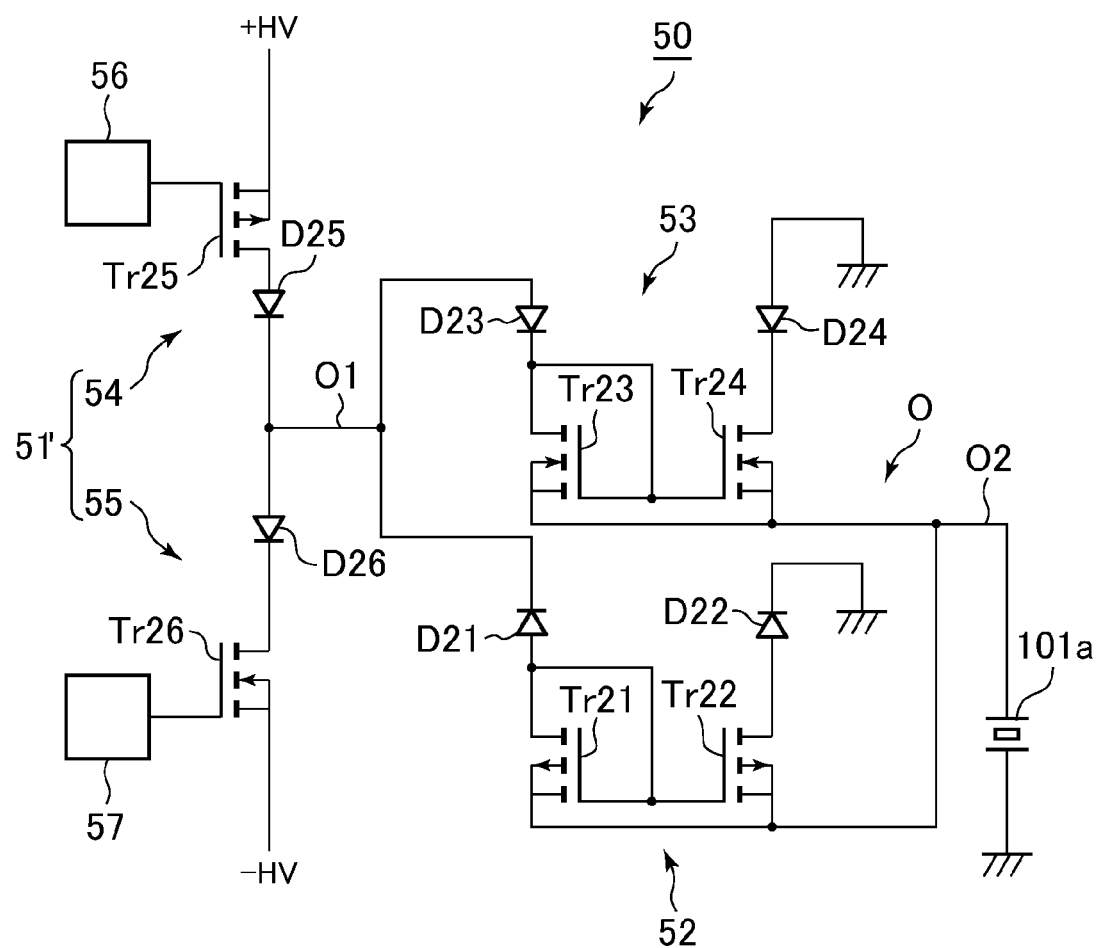
FIG. 19 is a circuit diagram showing an ultrasonic transducer driving circuit of a second example of modification to the second embodiment.

Then, a second modification example is described. In an ultrasonic transducer driving circuit 50 of the second modification example, instead of the voltage output type circuit 51, a voltage output type circuit 51' shown in FIG. 19 is connected to the output line O. The ultrasonic transducer driving circuit 50 of the second modification example outputs two levels of voltages as output voltages.

The voltage output type circuit 51' includes a positive voltage output circuit 54 and a negative voltage output circuit 55. Both the positive voltage output circuit 54 and the negative voltage output circuit 55 output a voltage to the output line O. The positive voltage output circuit 54 outputs a positive voltage to the output line O and the negative voltage output circuit 55 outputs a negative voltage to the output line O.

The positive voltage output circuit 54 includes a positive supply voltage +HV, a transistor Tr25, and a diode D25. The diode D25 is connected between the transistor Tr25 and the output line O.

The transistor Tr25 is a p-channel type MOSFET in which the positive supply voltage +HV is connected to its source terminal and the diode D2 is connected to its drain terminal To a gate terminal of the transistor Tr25, a first driver circuit 56 is connected that outputs a drive signal to turn the transistor Tr25 on/off.

The negative voltage output circuit 55 includes a negative supply voltage −HV, a transistor Tr26, and a diode D26. The diode D26 is connected between the transistor Tr26 and the output line O.

The negative voltage output circuit 55 is an n-channel MOSFET in which the negative supply voltage −HV is connected to its source terminal and the diode D26 is connected to its drain terminal To a gate terminal of the transistor Tr26, a second driver circuit 57 is connected that outputs a drive signal to turn the transistor Tr26 on/off.

How the circuit of the second modification example operates is described. At time t1, as shown in FIG. 12, the transistor Tr25 turns into an ON state. This produces a current I23 flowing through the transistor Tr23 and the voltage of the output line O rises.

Then, at time t2, the transistor Tr25 turns into an OFF state and the transistor Tr26 turns into an ON state. This causes a decrease in the voltage of the first output line O1, thereby producing currents I21 and I22 flowing through the transistors Tr21 and Tr22.

Then, at time t4, the transistor Tr26 turns into an OFF state and the transistor Tr25 turns into an ON state. This causes an increase in the voltage of the first output line O1, thereby producing currents I23, I24 flowing through the transistors Tr23, Tr24.

Third Embodiment

Next, a third embodiment is described. Ultrasonic transducer driving circuits 70 of the present example are provided in the transmitter unit 1021 of the ultrasonic image display apparatus 100 (see FIG. 1 and FIG. 2), as is the case for the ultrasonic transducer driving circuits 1 of the first embodiment and the ultrasonic transducer driving circuits 50 of the second embodiment.

Figure 20:
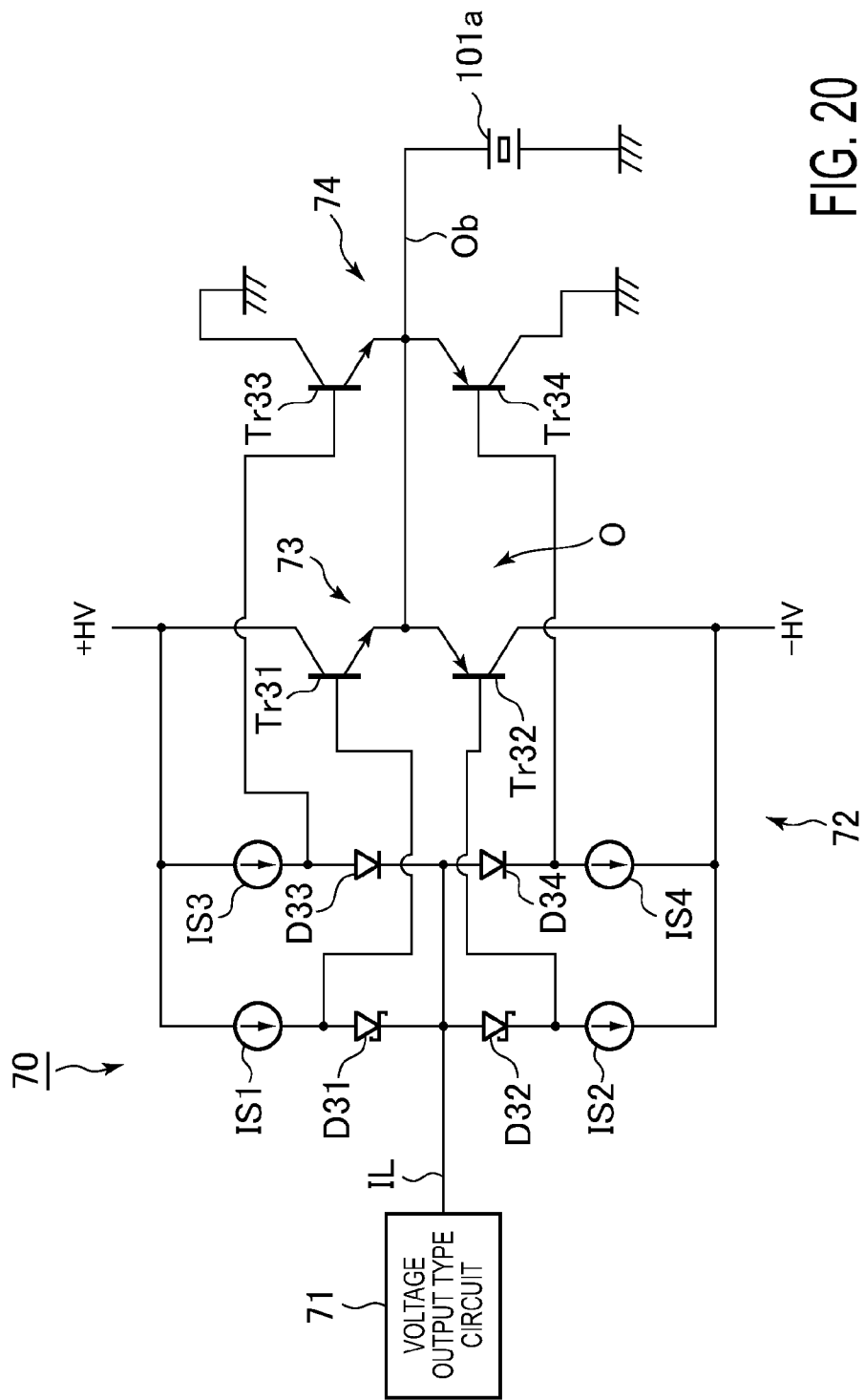
FIG. 20 is a circuit diagram showing an ultrasonic transducer driving circuit of a third embodiment.

As shown in FIG. 20, each of the ultrasonic transducer driving circuits 70 includes a voltage output type circuit 71 and a buffer amplifier 72. The voltage output type circuit 71 controls an output voltage of an output line O and supplies an electrical current to an output line O for driving the corresponding ultrasonic transducer 101a. This output line O corresponds to an output line of the voltage output type circuit 71. The output line O includes an output line of the ultrasonic transducer driving circuit 70. The output line O is one example of an embodiment of an output line.

Here, a detailed configuration of the voltage output type circuit 71 is not shown.

The buffer amplifier 72 is provided along the output line O of the voltage output type circuit 71. Here, the output line includes an input line IL to the buffer amplifier 72 and an output line Ob of the buffer amplifier 72. To the buffer amplifier 72, an output voltage of the voltage output type circuit 71 is input through the input line IL.

The output line Ob of the buffer amplifier 72 is also the output line of the ultrasonic transducer driving circuit 70.

The buffer amplifier 72 includes a first push-pull circuit 73 and a second push-pull circuit 74. The first push-pull circuit 73 is configured with transistors Tr31 and Tr32. The second push-pull circuit 74 is configured with transistors Tr33 and Tr34. The transistors Tr31 and Tr33 are npn type bipolar transistors. The transistors Tr32 and Tr34 are pnp type bipolar transistors.

The first push-pull circuit 73 is one example of an embodiment of a first push-pull circuit and the second push-pull circuit 74 is one example of an embodiment of a second push-pull circuit. Besides, the transistor Tr31 is one example of an embodiment of a first transistor and the transistor Tr32 is one example of an embodiment of a second transistor. Further, the transistor Tr33 is one example of an embodiment of a third transistor and the transistor Tr34 is one example of an embodiment of a fourth transistor.

In the first push-pull circuit 73, emitter terminals of the transistors Tr31 and Tr32 are connected to each other. In the second push-pull circuit 74, emitter terminals of the transistors Tr33 and Tr34 are connected to each other. The output line Ob of the buffer amplifier 72 is connected between the transistors Tr31 and Tr32, and between the transistors Tr33 and Tr34.

A positive supply voltage +HV is connected to a collector terminal of the transistor Tr31. A negative supply voltage −HV is connected to a collector terminal of the transistor Tr32.

Collector terminals of the transistors Tr33 and Tr34 are connected to a ground.

Between the positive supply voltage +HV and the input line IL, a current source IS1 and a schottky diode D31 are provided. The current source IS1 is arranged to the positive supply voltage +HV and the schottky diode D31 is arranged to the input line IL. A base terminal of the transistor Tr31 is connected between the current source IS1 and the schottky diode D31.

Between the negative supply voltage −HV and the input line IL, a current source IS2 and a schottky diode D32 are provided. The current source IS2 is arranged to the negative supply voltage −HV and the schottky diode D32 is arranged to the input line IL. A base terminal of the transistor Tr32 is connected between the current source IS2 and the schottky diode D32.

Between the positive supply voltage +HV and the input line IL, a current source IS3 and a diode 33 are also provided in parallel with the current source IS1 and the schottky diode D31. The current source IS3 is arranged to the positive supply voltage +HV and the diode D33 is arranged to the input line IL. A base terminal of the transistor Tr33 is connected between the current source IS3 and the diode D33.

Likewise, between the negative supply voltage −HV and the input line IL, a current source IS4 and a diode 34 are provided in parallel with the current source IS2 and the schottky diode D32. The current source IS3 is arranged to the negative supply voltage −HV and the diode D34 is arranged to the input line IL. A base terminal of the transistor Tr34 is connected between the current source IS4 and the diode D34.

To the transistors Tr31 to Tr34, a voltage having a predetermined difference relative to the voltage of the input line IL, that is, the output voltage of the voltage output type circuit 71 is input. For example, the potential of the base terminal of the transistor Tr31 is 0.3 V higher than the potential of the input line IL and the potential of the base terminal of the transistor Tr33 is 0.7 V higher than the potential of the input line IL. The potential of the base terminal of the transistor Tr32 is 0.3 V lower than the potential of the input line IL and the potential of the base terminal of the transistor Tr34 is 0.7 V lower than the potential of the input line IL.

The potential difference between the base terminal of the transistor Tr33 and the input line IL is larger than the potential difference between the base terminal of the transistor Tr31 and the input line IL. The potential difference between the base terminal of the transistor Tr34 and the input line IL is larger than the potential difference between the base terminal of the transistor Tr32 and the input line IL.

Due to the fact that the potential differences of the base terminals of the transistors Tr31, Tr33 and the input line IL are as above, when the output line Ob is at a negative voltage, the transistor Tr33, of the transistor Tr31 and the transistor Tr33, turns into an ON state in accordance with an output voltage of the voltage output type circuit 71, thereby allowing the current arising from electric charges accumulated in the ultrasonic transducer 101a to flow from ground to the output line Ob. Further details will be provided later.

Due to the fact that the potential differences of the base terminals of the transistors Tr32, Tr34 and the input line IL are as above, when the output line Ob is at a positive voltage, the transistor Tr34, of the transistor Tr32 and the transistor Tr34, turns into an ON state in accordance with an output voltage of the voltage output type circuit 71, thereby allowing the current arising from electric charges accumulated in the ultrasonic transducer 101a to flow from the output line Ob to ground. Further details will be provided later.

Figure 21:
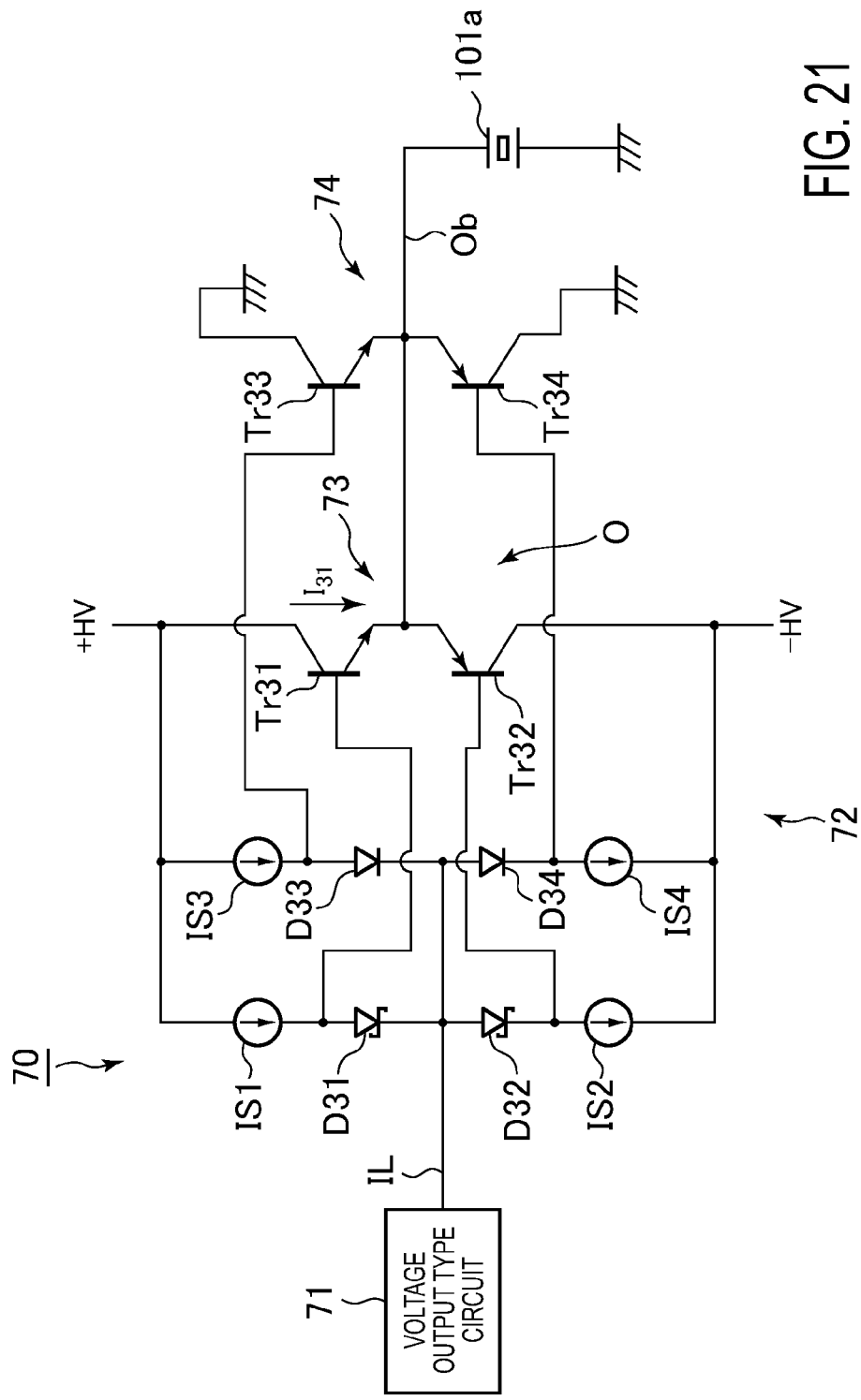
FIG. 21 is a diagram for explaining how the ultrasonic transducer driving circuit of the third embodiment operates.

Then, how the ultrasonic transducer driving circuit 70 operates is described. A voltage having a waveform that is shown in FIG. 12, as is the case for the second embodiment, is output from the voltage output type circuit 71. In a state in which the output line Ob is at a ground voltage, when an output voltage starts to be supplied from the voltage output type circuit 71 to the input line IL at time t1, the voltage of this input line IL rises. With the rise of the voltage of this input line IL, a base-emitter voltage of the transistor Tr31 rises and the transistor Tr31 turns into an ON state. This produces a current I31 flowing through the transistor Tr31, as shown in FIG. 21, and the voltage of the output line Ob rises.

Then, after the output voltage of the voltage output type circuit 71 has reached a peak at time t2, when it starts to fall, the transistor Tr31 turns into an OFF state due to a decrease in its base voltage. As the output voltage of the voltage output type circuit 71 falls, the base voltages of the transistors 32 and 34 fall. Because the turning of the transistor Tr31 into the OFF state stops the rise of the voltage of the output line Ob, the falling base voltages of the transistors Tr32 and Tr34 cause an increase in the potential difference of base terminal with respect to emitter terminal in the transistors Tr32 and Tr34.

Figure 22:
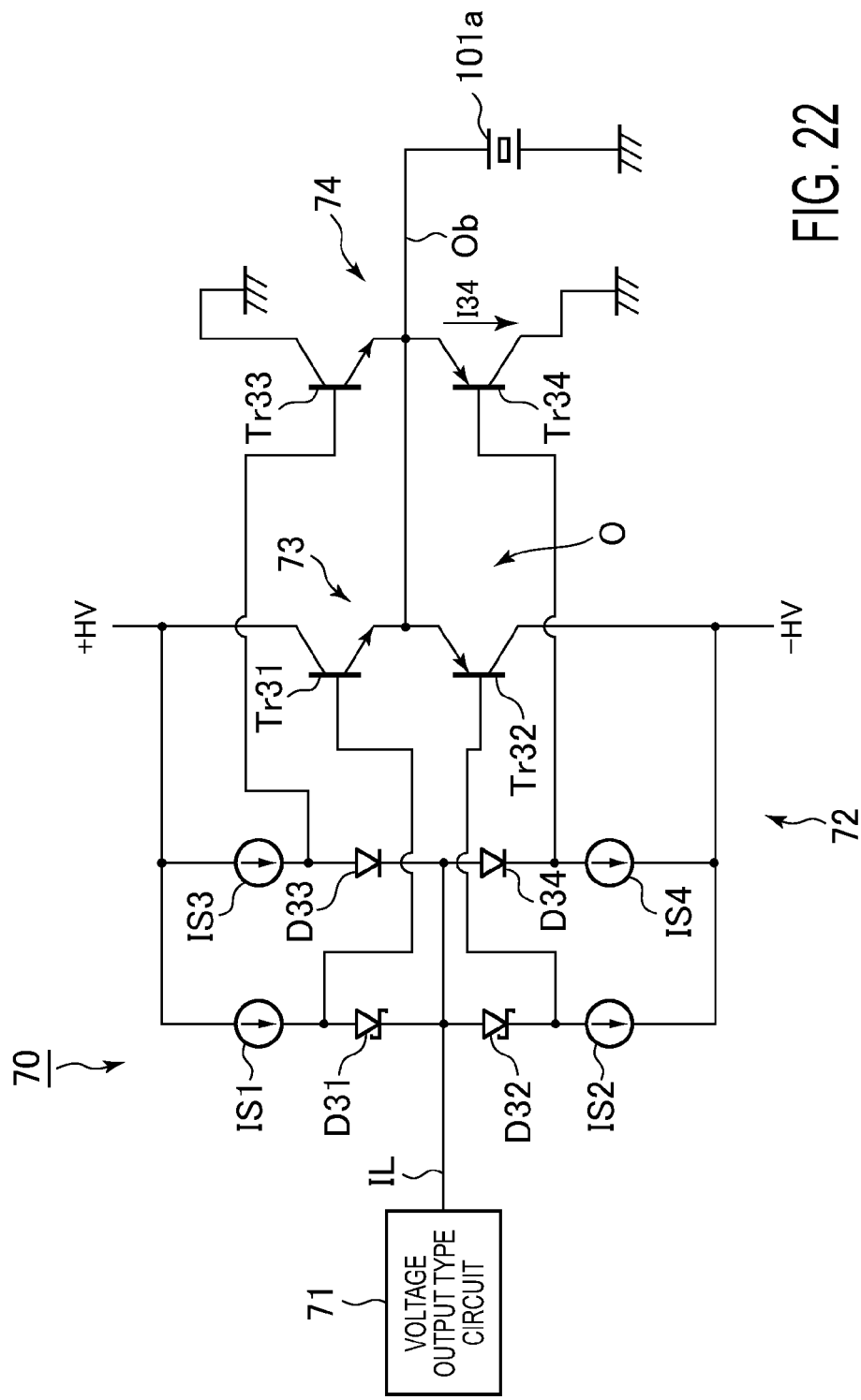
FIG. 22 is a diagram for explaining how the ultrasonic transducer driving circuit of the third embodiment operates.

Here, as mentioned above, the potential difference between the base terminal of the transistor Tr34 and the input line IL is larger than the potential difference between the base terminal of the transistor Tr32 and the input line IL. Therefore, the transistor Tr34 turns into an ON state earlier than the transistor Tr32, thereby producing a current I34 flowing through the transistor Tr34, as shown in FIG. 22.

Figure 23:
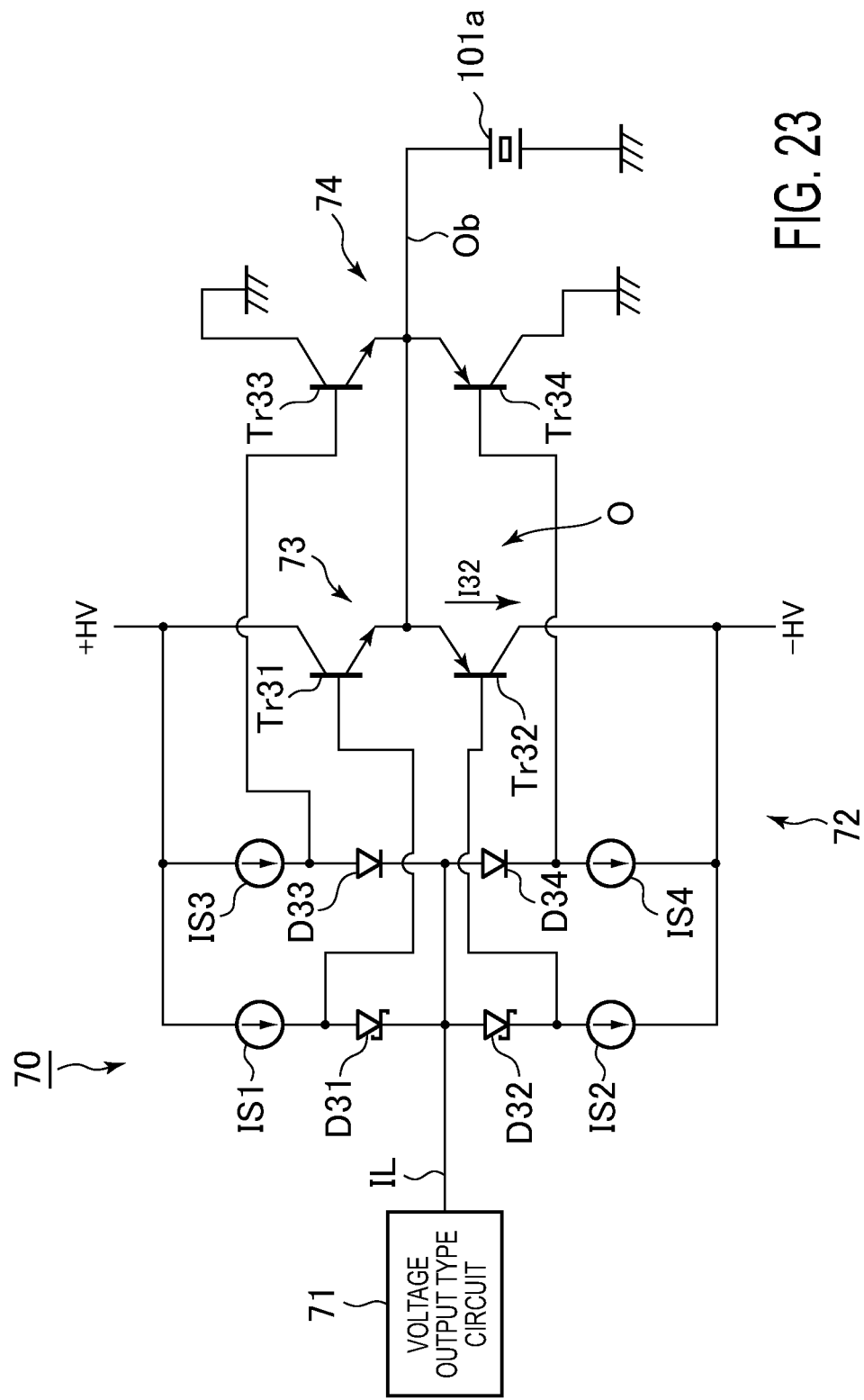
FIG. 23 is a diagram for explaining how the ultrasonic transducer driving circuit of the third embodiment operates.

After the transistor Tr34 has turned into the ON state, until the output voltage of the voltage output type circuit 71 comes to the ground voltage at time t3, the voltage of the input line IL and the voltage of the output line Ob fall in a state in which the voltage of the base terminal with respect to the emitter terminal of the transistor Tr34 is equal to the voltage of the base terminal of the transistor Tr34 with respect to the input line IL. After the output voltage of the voltage output type circuit 71 has come to the ground voltage at time t3, when it further falls, the voltage of the base terminal with respect to the emitter terminal of the transistor Tr32 falls and the transistor Tr32 turns into an ON state, as the voltage of the output line Ob remains at the ground voltage. This, in consequence, produces a current I32 flowing through the transistor Tr32, as shown in FIG. 23, and the voltage of the output line Ob falls.

Then, after the output voltage of the voltage output type circuit 71 has become minimum, when it starts to rise, the transistor Tr32 turns into an OFF state due to a rise of its base voltage. As the output voltage of the voltage output type circuit 71 rises, the base voltages of the transistors Tr31 and Tr33 rise. Because the turning of the transistor Tr32 into the OFF state stops the fall of the voltage of the output line Ob, the rising base voltages of the transistors Tr31 and Tr33 cause an increase in the potential difference of base terminal with respect to emitter terminal in the transistors Tr31 and Tr33.

Figure 24:
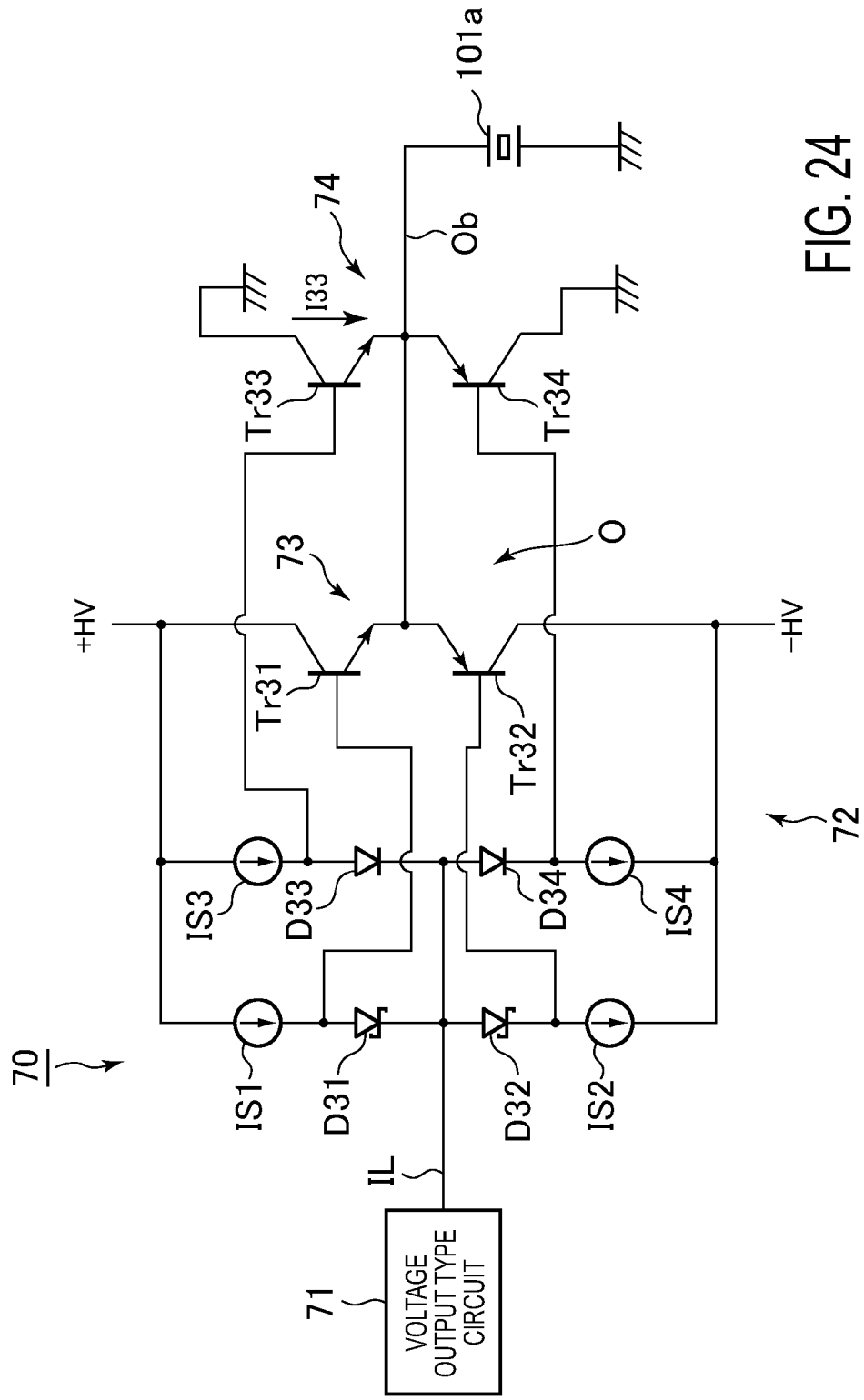
FIG. 24 is a diagram for explaining how the ultrasonic transducer driving circuit of the third embodiment operates.

Here, as mentioned above, the potential difference between the base terminal of the transistor Tr33 and the input line IL is larger than the potential difference between the base terminal of the transistor Tr31 and the input line IL. Therefore, the transistor Tr33 turns into an ON state earlier than the transistor Tr31, thereby producing a current I33 flowing through the transistor Tr33, as shown in FIG. 24.

After the transistor Tr33 has turned into the ON state, until the output voltage of the voltage output type circuit 71 comes to the ground voltage at time t4, the voltage of the input line IL and the voltage of the output line Ob rise in a state in which the voltage of the base terminal with respect to the emitter terminal of the transistor Tr33 is equal to the voltage of the base terminal of the transistor Tr33 with respect to the input line IL. After the output voltage of the voltage output type circuit 71 has come to the ground voltage at time t4, when it further rises, the voltage of the base terminal with respect to the emitter terminal of the transistor Tr31 rises and the transistor Tr31 turns into an ON state again, as the voltage of the output line Ob remains at the ground voltage.

According to the ultrasonic transducer driving circuit 50 of the present example, when the output line Ob is at a positive voltage, the current arising from electric charges accumulated in the ultrasonic transducer 101a flows from the output line Ob to ground as the current I34, due to the fact that the transistor Tr34 turns into an ON state. When the output line Ob is at a negative voltage, the current arising from electric charges accumulated in the ultrasonic transducer 101a flows from ground to the output line Ob as the current I33, due to the fact that the transistor Tr33 turns into an ON state.

Although the present invention has been described in accordance with the embodiments, it will be obvious that various modifications to the present invention may be made without changing the gist of the invention.

The invention claimed is:

1. An ultrasonic transducer driving circuit comprising:
a current output type circuit configured to output a controlled output current to an output line for driving an ultrasonic transducer, said current output type circuit comprising:
   a first current discharge circuit configured to allow a current arising from electric charges accumulated in the ultrasonic transducer to flow from an output line to ground when the output line is at a positive voltage;
   a second current discharge circuit configured to allow the current arising from the electric charges accumulated in the ultrasonic transducer to flow from ground to the output line when the output line is at a negative voltage;
   a positive current output type circuit configured to output a positive current, said positive current output type circuit comprising said second current discharge circuit and a positive current mirror circuit connected to a positive power supply, said positive current mirror circuit configured to output said positive current; and
   a negative current output type circuit configured to output a negative current, said negative current output type circuit comprising said first current discharge circuit and a negative current mirror circuit connected to a negative power supply, said negative current mirror circuit configured to output said negative current; and
a current control unit configured to output a current to said current output type circuit for controlling the output current, wherein said first current discharge circuit and said second current discharge circuit are controlled by a current from said current control unit.

2. The ultrasonic transducer driving circuit according to claim 1, wherein said current control unit comprises a current digital-to-analog converter (DAC) configured to output a current for controlling an output current of said current output type circuit.

3. The ultrasonic transducer driving circuit according to claim 1, wherein said current DAC comprises a positive current DAC connected to said positive current output type circuit and a negative DAC connected to said negative current output type circuit.

4. The ultrasonic transducer driving circuit according to claim 3, wherein:
   said positive current output type circuit comprises a positive current switching circuit connected to said positive current mirror circuit and said second current discharge circuit said positive current switching circuit configured to allow a current to flow through one of said positive current mirror circuit and said second current discharge circuit; and
   said negative current output type circuit comprises a negative current switching circuit connected to said negative current mirror circuit and said first current discharge circuit said negative switching circuit configured to allow a current to flow through one of said negative current mirror circuit and said first current discharge circuit.

5. The ultrasonic transducer driving circuit according to claim 1, wherein said first current discharge circuit and said second current discharge circuit each comprises a current mirror circuit including a pair of transistors connected to a ground.

6. An ultrasonic image display apparatus comprising an ultrasonic transducer driving circuit according to claim 1.

* * * * *